(12) United States Patent
Dioum et al.

(10) Patent No.: US 8,722,716 B2
(45) Date of Patent: May 13, 2014

(54) ISOXAZOLE TREATMENTS FOR DIABETES

(71) Applicant: The Board of Regents of the University of Texas System, Austin, TX (US)

(72) Inventors: Elhadij Dioum, Dallas, TX (US); Jay Schneider, Coppell, TX (US); Doug Frantz, Flower Mound, TX (US); Hector Aguilar, San Antonio, TX (US); Melanie Cobb, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/683,907

(22) Filed: Nov. 21, 2012

(65) Prior Publication Data

US 2013/0178506 A1    Jul. 11, 2013

Related U.S. Application Data

(60) Provisional application No. 61/563,419, filed on Nov. 23, 2011, provisional application No. 61/566,056, filed on Dec. 2, 2011.

(51) Int. Cl.
*C07D 413/04* (2006.01)
*C07D 261/18* (2006.01)

(52) U.S. Cl.
USPC .......................... 514/378; 435/375; 548/248

(58) Field of Classification Search
None
See application file for complete search history.

(56) References Cited

U.S. PATENT DOCUMENTS

| | | | |
|---|---|---|---|
| 5,001,124 | A | 3/1991 | Patterson et al. |
| 7,981,935 | B2 | 7/2011 | Olson et al. |
| 8,193,225 | B2 | 6/2012 | Schneider et al. |
| 8,318,951 | B2 | 11/2012 | Olson et al. |
| 2006/0036451 | A1 | 4/2006 | Liu et al. |
| 2008/0070922 | A1 | 3/2008 | Burkey et al. |
| 2009/0036451 | A1 | 2/2009 | Schneider et al. |
| 2013/0143885 | A1 | 6/2013 | Schneider et al. |
| 2013/0143935 | A1 | 6/2013 | Olson et al. |

FOREIGN PATENT DOCUMENTS

| | | |
|---|---|---|
| DE | 10 2004 054 666 | 5/2006 |
| JP | 08-0274130 | 1/1996 |
| WO | WO 2007/007919 | 1/2007 |

OTHER PUBLICATIONS

Morissette, et al., "High-throughput crystallization: polymorphs, salts, co-crystals and solvates of pharmaceutical solids", *Advanced Drug Delivery Reviews*, 56(3):275-300, 2004.
Office Action Issued in U.S. Appl. No. 11/947,479, Dated Aug. 16, 2011.
Office Action Issued in U.S. Appl. No. 11/974,479, Dated Sep. 1, 2010.
Office Action Issued in U.S. Appl. No. 11/974,479, Dated Dec. 17, 2009.
Office Action Issued in U.S. Appl. No. 12/183,884, Dated Jan. 10, 2011.
Office Action Issued in U.S. Appl. No. 13/116,574, Dated Jan. 26, 2012.
Office Action Issued in U.S. Appl. No. 13/116,574, Dated Nov. 10, 2011.
Office Action Issued in U.S. Appl. No. 13/487,963, Dated Apr. 29, 2013.
Office Action Issued in U.S. Appl. No. 13/674,710, Dated Aug. 1, 2013.
PCT International Search Report and Written Opinion issued in International Application No. PCT/US2012/66346, mailed Jan. 31, 2013.
Rawat, et al., "Study of photochomism in benzenesulfonylhydrazones", *Chemical Abstracts*, 110:74706, 1989.
Registry No. 857283-79-5, entered into Registry File on STN on Jul. 25, 2005.
Registry No. 921177-00-6, entered into Registry File on STN on Feb. 15, 2007.
Registry No. 922343-19-9, entered into Registry File on STN on Feb. 22, 2007.
Russell, et al., "Regulated expression of pH sensing G protein-coupled receptor-68 identified through chemical biology defines a new drug target for ischemic heart disease", *ACS Chem. Biol.*, 7(6):1077-1083, 2012.
Russell, et al., "Targeting native adult heart progenitors with cardiogenic small-molecules", *ACS Chem. Biol.*, 7(6):1067-1076, 2012.
Sadek, et al., "Cardiogenic small molecules that enhance myocardial repair by stem cells", *Proc. Natl. Acad. Sci.*, 105(16):6063-6068, 2008.
Schneider, et al., "Small-molecule activation of neuronal cell fate", *Nat. Chem. Bio.*, 4(7):408-410, 2008.
Souillac, et al., "Characterization of delivery systems, differential scanning calorimetry," *Encyclopedia of Controlled Drug Delivery*, John Wiley & Sons, pp. 212-227, 1999.
Vippagunta, et al., "Crystalline solids," *Advanced Drug Delivery Reviews*, 48:3-26, 2001.

*Primary Examiner* — Kamal Saeed
(74) *Attorney, Agent, or Firm* — Parker Highlander PLLC

(57) ABSTRACT

The present invention relates to compounds and methods for inducing synthesis and secretion of insulin from pancreatic beta cells. The methods may take place in vitro, ex vivo such as in isolates from adult mammalian tissue, or in vivo. Compounds and methods described herein may find use in the treatment of diabetes.

21 Claims, 19 Drawing Sheets

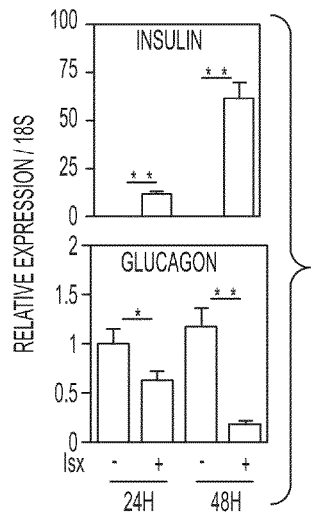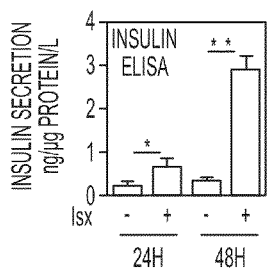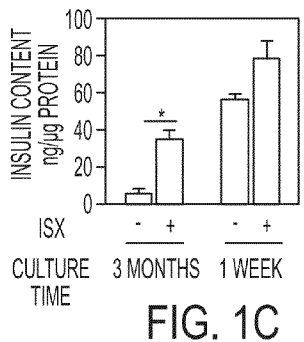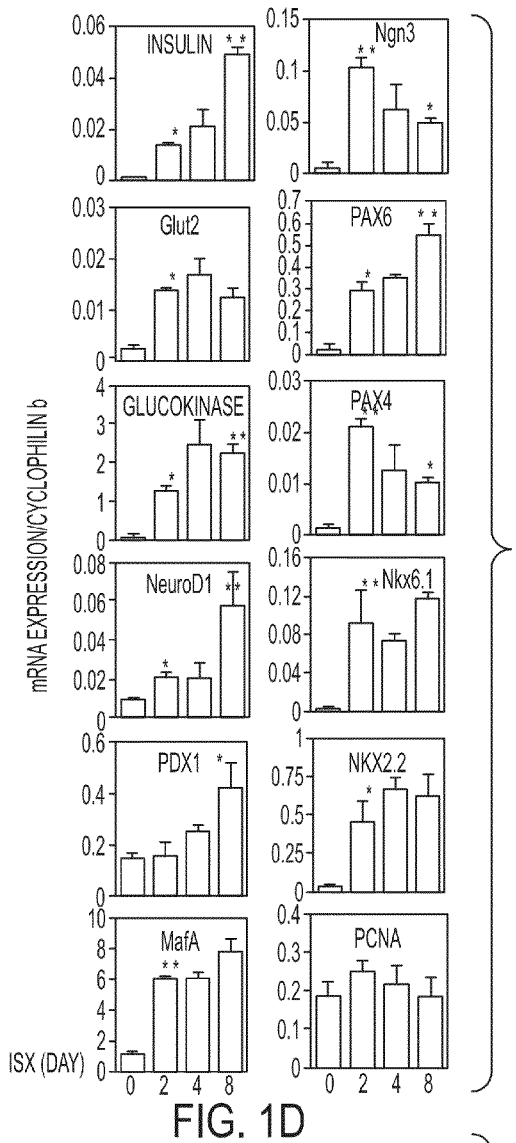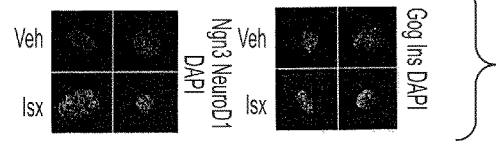
FIG. 1A
FIG. 1B
FIG. 1C
FIG. 1D
FIG. 1E

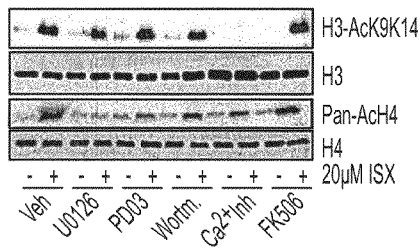
FIG. 4A
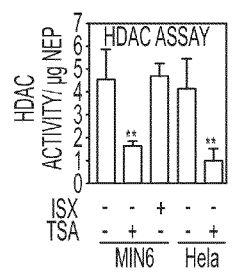 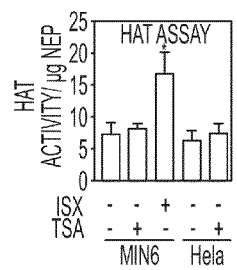 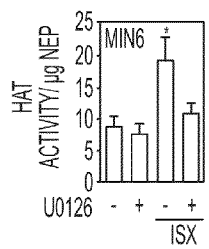
FIG. 4B  FIG. 4C  FIG. 4D
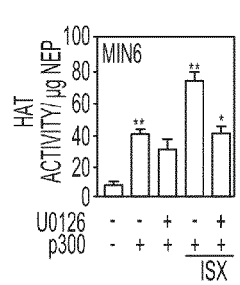 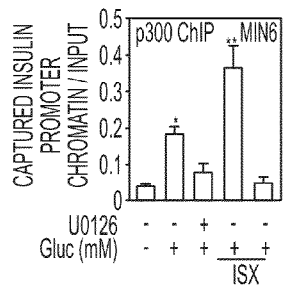
FIG. 4E  FIG. 4F
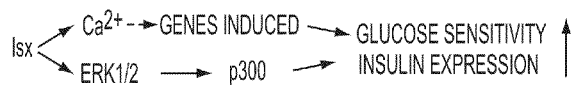
FIG. 4G

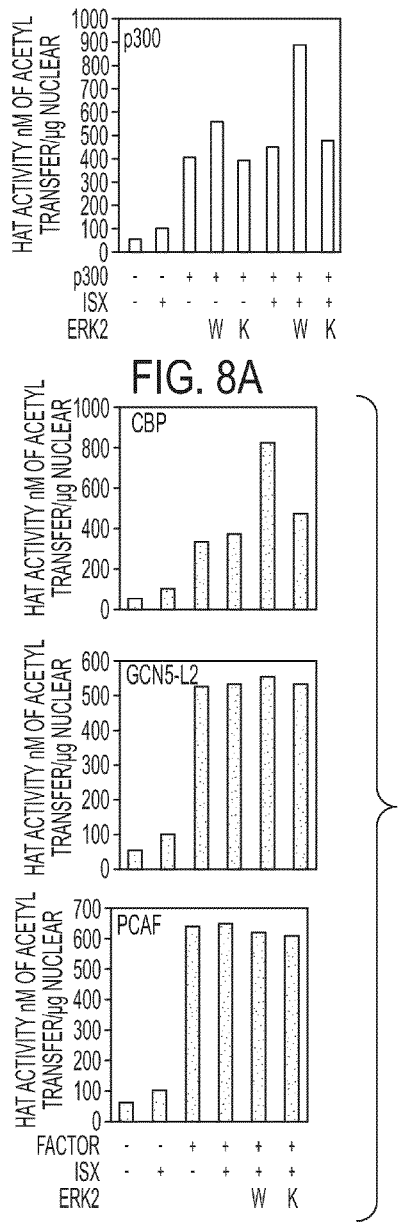
FIG. 8A
FIG. 8B
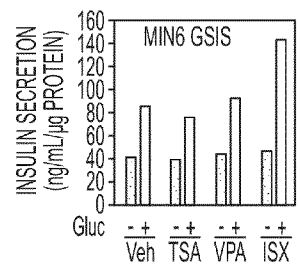
FIG. 8C
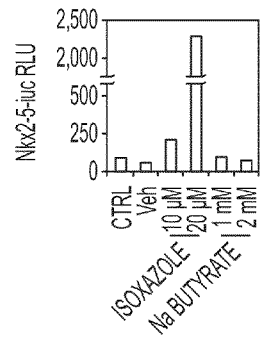
FIG. 8D

ISOXAZOLE TREATMENTS FOR DIABETES

This application claims benefit of priority to U.S. Provisional Application Ser. Nos. 61/563,419, filed Nov. 23, 2011, and 61/566,056, filed Dec. 2, 2011, the entire contents of both applications being incorporated by reference herein.

The invention was made with government support under NIH P60 DK079626, R37 DK34128 and R01 DK55310 awarded by the National Institutes of Health. The government has certain rights in the invention.

BACKGROUND OF THE INVENTION

1. Field of the Invention

The present invention relates generally to the fields of cell biology, developmental biology and medicine. More particularly, it concerns methods and compositions relating to the stimulation of insulin production and the treatment of diabetes.

2. Description of Related Art

Nearly one-third of the adult population of the United States is at risk for type 2 diabetes because of abnormal glucose tolerance or abnormally high fasting glucose (Genuth et al., 2003). Type 2 diabetes is increasing at an alarming rate and is now found not only in adults but also in chronically overweight children. Pancreatic β cells play a unique role in glucose homeostasis by secreting insulin when the concentrations of glucose and other nutrients in the circulation rise (Newgard and McGarry, 1995). Insulin facilitates proper nutrient utilization and storage by most tissues. Beta cells are vulnerable to persistent nutrient excess from secretory stress. During the development of type 2 diabetes, pancreatic beta cells become progressively unable to produce and secrete sufficient insulin to prevent hyperglycemia (Genuth et al., 2003; Muoio and Newgard, 2008; Rutter and Parton, 2008). Identifying strategies to maintain euglycemia is essential to limit diabetes and its destructive consequences (Halban et al., 2010; Borowiak and Melton, 2009).

Nutrients regulate insulin production at several steps in the biosynthetic pathway in addition to its secretion, including cleavage of the preprohormone, translation, and transcription (Redmon et al., 1994; Xu et al., 1998; Wicksteed et al., 2007; Steiner et al., 2009; Goodge and Hutton, 2000). The immediate events to replenish secreted insulin involve translation of pre-existing mRNA and hormone processing. On a longer time scale, new insulin gene transcription maintains the pool of mRNA for translation on demand.

Insulin gene transcription is regulated by the cooperation of a group of glucose-sensitive transcription factors expressed in a tissue-restricted manner (Ohneda et al., 2000; Aramata et al., 2005). Among the most important of these, the basic-loop-helix (bHLH) factor BETA2 (also known as NeuroD1), the homeodomain factor PDX-1, and the basic leucine zipper factor MafA have been shown to activate the insulin gene promoter synergistically and are essential for glucose-stimulated insulin gene transcription. Mutations in PDX-1 and BETA2 have been linked to maturity onset diabetes of the young (MODY) and are classified as MODY4 and MODY6 genes, respectively (Habener and Stoffers, 1998; Vaxillaire and Froguel, 2008).

BETA2 is required during neuronal development for the differentiation of neuronal progenitor cells in the central and peripheral nervous system (Kageyama et al., 1997; Chae et al., 2004). BETA2 also has an essential role in the development of neuroendocrine cells in other organs including lung, intestine, and pancreas. In the adult, the main function of BETA2 is in pancreatic β cells, although it is also required for continued neurogenesis in the hippocampal CA1 region of the brain. The neurogenin (Ngn) family of bHLH proteins are direct transcriptional regulators of BETA2 during neuronal and pancreatic development (Huang et al., 2000; Sommer et al., 1996). While Ngn1 and 2 act exclusively in neuronal lineages, Ngn3 is the family member that induces BETA2 expression in pancreatic β cells. Several studies have reported that expression of one or more of these factors helps to promote differentiation of pancreatic endocrine cells from various stem cell populations (Borowiak and Melton, 2009; Gasa et al., 2004). However, the precise role played in pancreatic development is not understood.

SUMMARY OF THE INVENTION

Thus, in accordance with the present invention, there is provided a method of inducing insulin production and/or secretion from an islet β-cell comprising contacting said cell with a compound of formula (I):

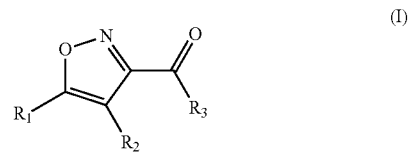

wherein:

$R_1$ is substituted or unsubstituted phenyl, substituted or unsubstituted thiophenyl or a substituent of formula (A):

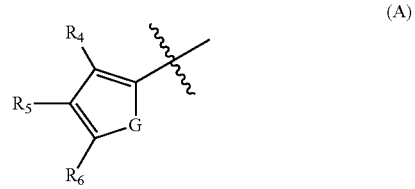

wherein:

$R_4$, $R_5$ and $R_6$ are each independently hydrogen, hydroxy, halo, cyano, nitro; or alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and G is O, —NH, or S;

$R_2$ is:

hydrogen, hydroxy, halo, or nitro; or alkyl$_{(C\leq10)}$, alkenyl$_{(C\leq10)}$, alkynyl$_{(C\leq10)}$, alkoxy$_{(C\leq10)}$, alkenyloxy$_{(C\leq10)}$, alkynyloxy$_{(C\leq10)}$, aryl$_{(C\leq12)}$, aralkyl$_{(C\leq15)}$, acyl$_{(C\leq10)}$, or a substituted version of any of these groups; or —C(O)R$_7$, —OC(O)R$_7$, —OC(O)OR$_7$, —C(O)NR$_8$R$_9$, —OC(O)NR$_8$R$_9$, —NR$_8$OR$_9$, or —SO$_3$R$_7$; wherein $R_7$ is hydrogen, alkyl$_{(C\leq10)}$, aryl$_{(C\leq12)}$, aralkyl$_{(C\leq15)}$;

$R_8$ and $R_9$ are each independently hydrogen, alkyl$_{(C\leq10)}$, aryl$_{(C\leq12)}$, aralkyl$_{(C\leq15)}$, or taken together are alkanediyl$_{(C\leq6)}$;

$R_3$ is —NH—O-alkyl$_{(C\leq10)}$, —NHOH, —OR$_{10}$ or —NR$_{11}$R$_{12}$, wherein $R_{10}$ is hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$;

$R_{11}$ and $R_{12}$ are each independently hydrogen, substituted or unsubstituted alkyl$_{(C\leq10)}$, substituted or unsubstituted alkenyl$_{(C\leq10)}$, substituted or unsubstituted alkynyl$_{(C\leq10)}$, aryl$_{(C≤12)}$, or aralkyl$_{(C≤15)}$; or $R_{11}$ and $R_{12}$ are taken together to form alkanediyl$_{(C≤6)}$, —CH$_2$CH$_2$NHCH$_2$CH$_2$—, or —CH$_2$CH$_2$OCH$_2$CH$_2$—; or $R_{11}$ and $R_{12}$ are taken together to form alkanediyl$_{(C≤6)}$;

or pharmaceutically acceptable salt thereof.

In particular combinations, $R_1$ is a substituent of formula (A), further G may be S, and further $R_4$, $R_5$ or $R_6$ may be hydrogen, including where $R_4$, $R_5$ and $R_6$ are each hydrogen.

In any of the preceding embodiments, $R_2$ may be hydrogen.

In any of the preceding embodiments, $R_3$ may be —NR$_{11}$R$_{12}$, including where $R_{12}$ or $R_{13}$ is cyclopropyl, cyclobutyl, cyclopentyl or cyclohexyl, and in particular where $R_{12}$ or $R_{13}$ is cyclopropyl.

The method may further employ a compound of formula (II):

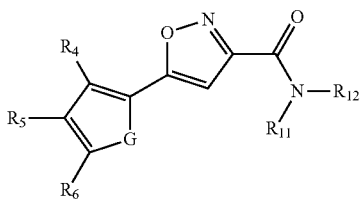

wherein:

$R_{11}$ and $R_{12}$ are both hydrogen; or $R_{11}$ is hydrogen and $R_{12}$ is substituted or unsubstituted alkyl$_{(C≤10)}$, substituted or unsubstituted alkenyl$_{(C≤10)}$, substituted or unsubstituted alkynyl$_{(C≤10)}$, or benzyl; or $R_{11}$ and $R_{12}$ taken together are —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$NHCH$_2$CH$_2$—, or —CH$_2$CH$_2$OCH$_2$CH$_2$—;

$R_4$, $R_5$ and $R_6$ are each independently:

hydrogen, halo, hydroxy, cyano, nitro; or alkyl$_{(C≤10)}$, aryl$_{(C≤12)}$, aralkyl$_{(C≤15)}$, heteroaryl$_{(C≤12)}$, acyl$_{(C≤10)}$ or a substituted version of any of these groups; and G is O, NH, or S, or a pharmaceutically acceptable salt thereof. Where G is S, $R_4$, $R_5$ or $R_6$ may in particular be hydrogen, including where $R_4$, $R_5$ and $R_6$ are each hydrogen.

In any of the preceding embodiments, $R_{11}$ may be hydrogen.

In any of the preceding embodiments, $R_{12}$ may be cyclopropyl or an aliphatic$_{(C≤10)}$ alcohol or an aliphatic$_{(C≤10)}$ polyol.

A particular example of the compound is:

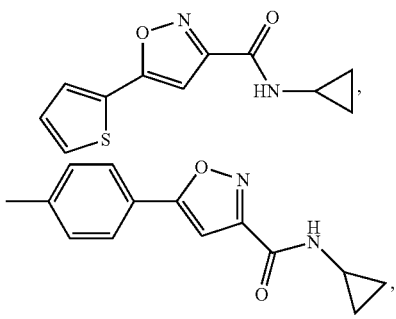

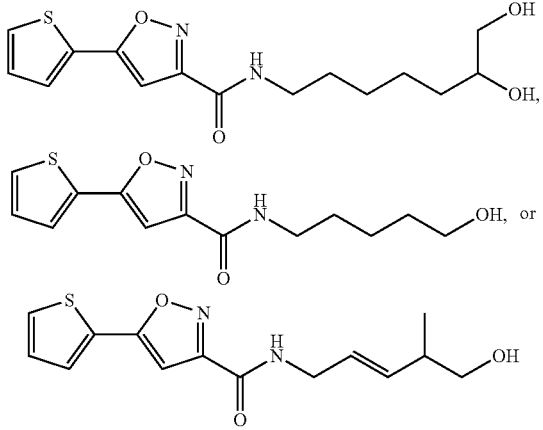

or a pharmaceutically acceptable salt thereof.

In any of the preceding embodiments, the cell is located in an animal subject.

In any of the preceding embodiments, the cell is contacted ex vivo.

In another embodiment, there is provided A method of treating diabetes in a subject comprising administering to said subject a compound of formula (I):

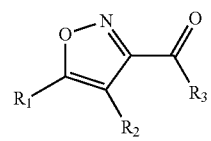

wherein:

$R_1$ is substituted or unsubstituted phenyl, substituted or unsubstituted thiophenyl or a substituent of formula (A):

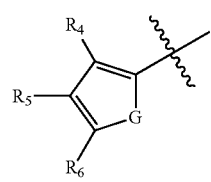

wherein:

$R_4$, $R_5$ and $R_6$ are each independently hydrogen, hydroxy, halo, cyano, nitro; or alkyl$_{(C≤10)}$, aryl$_{(C≤12)}$, aralkyl$_{(C≤15)}$, heteroaryl$_{(C≤12)}$, acyl$_{(C≤10)}$ or a substituted version of any of these groups; and G is O, —NH, or S;

$R_2$ is:

hydrogen, hydroxy, halo, or nitro; or alkyl$_{(C≤10)}$, alkenyl$_{(C≤10)}$, alkynyl$_{(C≤10)}$, alkoxy$_{(C≤10)}$, alkenyloxy$_{(C≤10)}$, alkynyloxy$_{(C≤10)}$, aryl$_{(C≤12)}$, aralkyl$_{(C≤15)}$, acyl$_{(C≤10)}$, or a substituted version of any of these groups; or —C(O)R$_7$, —OC(O)R$_7$, —OC(O)OR$_7$, —C(O)NR$_8$R$_9$, —OC(O)NR$_8$R$_9$, —NR$_8$OR$_9$, or —SO$_3$R$_7$; wherein $R_7$ is hydrogen, alkyl$_{(C≤10)}$, aryl$_{(C≤12)}$, aralkyl$_{(C≤15)}$;

$R_8$ and $R_9$ are each independently hydrogen, alkyl$_{(C≤10)}$, aryl$_{(C≤12)}$, aralkyl$_{(C≤15)}$, or taken together are alkanediyl$_{(C≤6)}$;

$R_3$ is —NH—O-alkyl$_{(C≤10)}$, —NHOH, —OR$_{10}$ or —NR$_{11}$R$_{12}$, wherein R$_{10}$ is hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$;

R$_{11}$ and R$_{12}$ are each independently hydrogen, substituted or unsubstituted alkyl$_{(C\leq10)}$, substituted or unsubstituted alkenyl$_{(C\leq10)}$, substituted or unsubstituted alkynyl$_{(C\leq10)}$, aryl$_{(C\leq12)}$, or aralkyl$_{(C\leq15)}$; or R$_{11}$ and R$_{12}$ are taken together to form alkanediyl$_{(C\leq6)}$, —CH$_2$CH$_2$NHCH$_2$CH$_2$—, or —CH$_2$CH$_2$OCH$_2$CH$_2$—; or R$_{11}$ and R$_{12}$ are taken together to form alkanediyl$_{(C\leq6)}$;

or pharmaceutically acceptable salt thereof.

In particular combinations, R$_1$ is a substituent of formula (A), further G may be S, and further R$_4$, R$_5$ or R$_6$ may be hydrogen, including where R$_4$, R$_5$ and R$_6$ are each hydrogen.

In any of the preceding embodiments, R$_2$ may be hydrogen.

In any of the preceding embodiments, R$_3$ may be —NR$_{11}$R$_{12}$, including where R$_{12}$ or R$_{13}$ is cyclopropyl, cyclobutyl, cyclopentyl or cyclohexyl, and in particular where R$_{12}$ or R$_{13}$ is cyclopropyl.

The method may further employ a compound of formula (II):

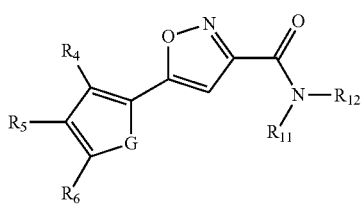

(II)

wherein:

R$_{11}$ and R$_{12}$ are both hydrogen; or R$_{11}$ is hydrogen and R$_{12}$ is substituted or unsubstituted alkyl$_{(C\leq10)}$, substituted or unsubstituted alkenyl$_{(C\leq10)}$, substituted or unsubstituted alkynyl$_{(C\leq10)}$, or benzyl; or R$_{11}$ and R$_{12}$ taken together are —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$NHCH$_2$CH$_2$—, or —CH$_2$CH$_2$OCH$_2$CH$_2$—;

R$_4$, R$_5$ and R$_6$ are each independently:

hydrogen, halo, hydroxy, cyano, nitro; or alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and G is O, NH, or S, or a pharmaceutically acceptable salt thereof. Where G is S, R$_4$, R$_5$ or R$_6$ may in particular be hydrogen, including where R$_4$, R$_5$ and R$_6$ are each hydrogen.

In any of the preceding embodiments, R$_{11}$ may be hydrogen.

In any of the preceding embodiments, R$_{12}$ may be cyclopropyl or an aliphatic$_{(C\leq10)}$ alcohol or an aliphatic$_{(C\leq10)}$ polyol.

A particular example of the compound is:

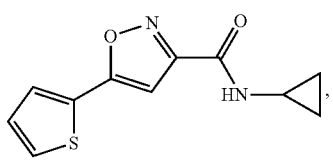

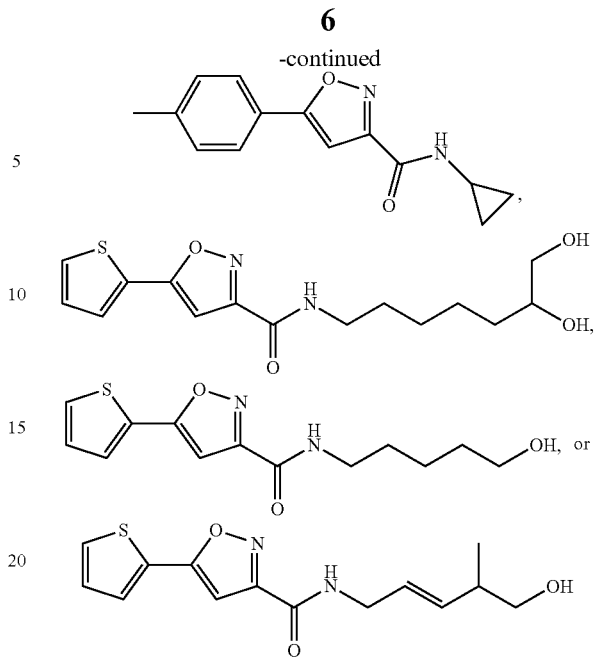

or a pharmaceutically acceptable salt thereof.

In any of the preceding embodiments, the cell is located in an animal subject.

In any of the preceding embodiments, the cell is contacted ex vivo.

A method of treating diabetes in a subject comprising (a) contacting an islet β-cell ex vivo with a compound of formula (I) and (b) administering said islet β-cell to said subject, wherein formula (I) is:

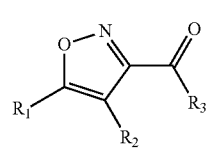

(I)

wherein:

R$_1$ is substituted or unsubstituted phenyl, substituted or unsubstituted thiophenyl or a substituent of formula (A):

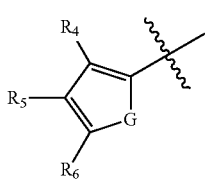

(A)

wherein:

R$_4$, R$_5$ and R$_6$ are each independently hydrogen, hydroxy, halo, cyano, nitro; or alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and G is O, —NH, or S;

R$_2$ is:

hydrogen, hydroxy, halo, or nitro; or alkyl$_{(C\leq10)}$, alkenyl$_{(C\leq10)}$, alkynyl$_{(C\leq10)}$, alkoxy$_{(C\leq10)}$, alkenyloxy$_{(C\leq10)}$, alkynyloxy$_{(C\leq10)}$, aryl$_{(C\leq12)}$, aralkyl$_{(C\leq15)}$, acyl$_{(C\leq10)}$, or a substituted version of any of these groups; or —C(O)R$_7$, —OC(O)R$_7$, —OC(O)OR$_7$, —C(O)NR$_8$R$_9$, —OC(O) NR$_8$R$_9$, —NR$_8$OR$_9$, or —SO$_3$R$_7$; wherein R$_7$ is hydrogen, alkyl$_{(C\leq10)}$, aryl$_{(C\leq12)}$, aralkyl$_{(C\leq15)}$;

R$_8$ and R$_9$ are each independently hydrogen, alkyl$_{(C\leq10)}$, aryl$_{(C\leq12)}$, aralkyl$_{(C\leq15)}$, or taken together are alkanediyl$_{(C\leq6)}$;

R$_3$ is —NH—O-alkyl$_{(C\leq10)}$, —NHOH, —OR$_{10}$ or —NR$_{11}$R$_{12}$, wherein R$_{10}$ is hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$;

R$_{11}$ and R$_{12}$ are each independently hydrogen, substituted or unsubstituted alkyl$_{(C\leq10)}$, substituted or unsubstituted alkenyl$_{(C\leq10)}$, substituted or unsubstituted alkynyl$_{(C\leq10)}$, aryl$_{(C\leq12)}$, or aralkyl$_{(C\leq15)}$; or R$_{11}$ and R$_{12}$ are taken together to form alkanediyl$_{(C\leq6)}$, —CH$_2$CH$_2$NHCH$_2$CH$_2$—, or —CH$_2$CH$_2$OCH$_2$CH$_2$—; or R$_{11}$ and R$_{12}$ are taken together to form alkanediyl$_{(C\leq6)}$; or pharmaceutically acceptable salt thereof.

In particular combinations, R$_1$ is a substituent of formula (A), further G may be S, and further R$_4$, R$_5$ or R$_6$ may be hydrogen, including where R$_4$, R$_5$ and R$_6$ are each hydrogen.

In any of the preceding embodiments, R$_2$ may be hydrogen.

In any of the preceding embodiments, R$_3$ may be —NR$_{11}$R$_{12}$, including where R$_{12}$ or R$_{13}$ is cyclopropyl, cyclobutyl, cyclopentyl or cyclohexyl, and in particular where R$_{12}$ or R$_{13}$ is cyclopropyl.

The method may further employ a compound of formula (II):

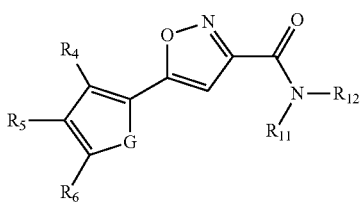

wherein:

R$_{11}$ and R$_{12}$ are both hydrogen; or R$_{11}$ is hydrogen and R$_{12}$ is substituted or unsubstituted alkyl$_{(C\leq10)}$, substituted or unsubstituted alkenyl$_{(C\leq10)}$, substituted or unsubstituted alkynyl$_{(C\leq10)}$, or benzyl; or R$_{11}$ and R$_{12}$ taken together are —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$NHCH$_2$CH$_2$—, or —CH$_2$CH$_2$OCH$_2$CH$_2$—;

R$_4$, R$_5$ and R$_6$ are each independently:

hydrogen, halo, hydroxy, cyano, nitro; or alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and G is O, NH, or S, or a pharmaceutically acceptable salt thereof. Where G is S, R$_4$, R$_5$ or R$_6$ may in particular be hydrogen, including where R$_4$, R$_5$ and R$_6$ are each hydrogen.

In any of the preceding embodiments, R$_{11}$ may be hydrogen.

In any of the preceding embodiments, R$_{12}$ may be cyclopropyl or an aliphatic$_{(C\leq10)}$ alcohol or an aliphatic$_{(C\leq10)}$ polyol.

A particular example of the compound is:

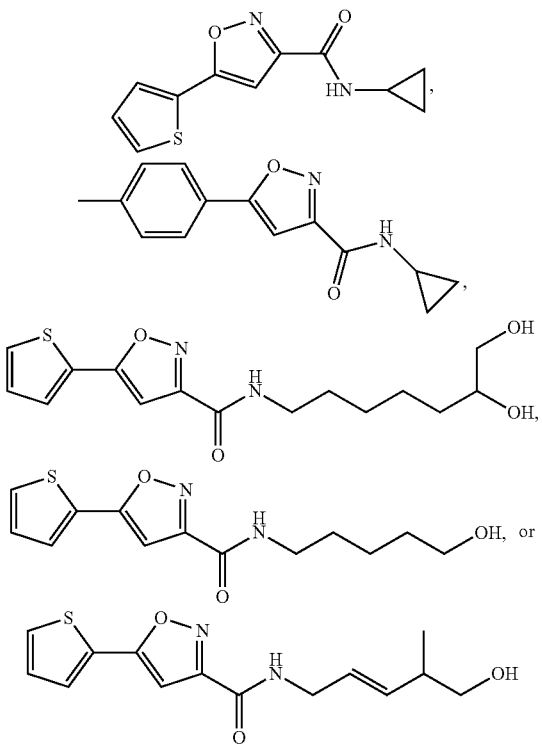

or a pharmaceutically acceptable salt thereof.

In still yet another embodiment, there is provided a method of reactivating an islet β-cell comprising contacting said cell with a compound of formula (I):

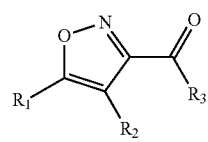

wherein:

R$_1$ is substituted or unsubstituted phenyl, substituted or unsubstituted thiophenyl or a substituent of formula (A):

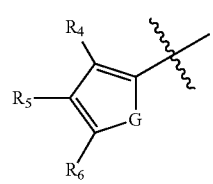

wherein:

R$_4$, R$_5$ and R$_6$ are each independently hydrogen, hydroxy, halo, cyano, nitro; or alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and G is O, —NH, or S;

R$_2$ is:

hydrogen, hydroxy, halo, or nitro; or alkyl$_{(C\leq10)}$, alkenyl$_{(C\leq10)}$, alkynyl$_{(C\leq10)}$, alkoxy$_{(C\leq10)}$, alkenyloxy$_{(C\leq10)}$, alkynyloxy$_{(C≤10)}$, aryl$_{(C≤12)}$, aralkyl$_{(C≤15)}$, acyl$_{(C≤10)}$, or a substituted version of any of these groups; or —C(O)R$_7$, —OC(O)R$_7$, —OC(O)OR$_7$, —C(O)NR$_8$R$_9$, —OC(O)NR$_8$R$_9$, —NR$_8$OR$_9$, or —SO$_3$R$_7$; wherein R$_7$ is hydrogen, alkyl$_{(C≤10)}$, aryl$_{(C≤12)}$, aralkyl$_{(C≤15)}$;

R$_8$ and R$_9$ are each independently hydrogen, alkyl$_{(C≤10)}$, aryl$_{(C≤12)}$, aralkyl$_{(C≤15)}$, or taken together are alkanediyl$_{(C≤6)}$;

R$_3$ is —NH—O-alkyl$_{(C≤10)}$, —NHOH, —OR$_{10}$ or —NR$_{11}$R$_{12}$, wherein R$_{10}$ is hydrogen, substituted or unsubstituted alkyl$_{(C≤10)}$, substituted or unsubstituted alkenyl$_{(C≤10)}$, substituted or unsubstituted alkynyl$_{(C≤10)}$, substituted or unsubstituted aryl$_{(C≤12)}$, or substituted or unsubstituted aralkyl$_{(C≤15)}$;

R$_{11}$ and R$_{12}$ are each independently hydrogen, substituted or unsubstituted alkyl$_{(C≤10)}$, substituted or unsubstituted alkenyl$_{(C≤10)}$, substituted or unsubstituted alkynyl$_{(C≤10)}$, aryl$_{(C≤12)}$, or aralkyl$_{(C≤15)}$; or R$_{11}$ and R$_{12}$ are taken together to form alkanediyl$_{(C≤6)}$, —CH$_2$CH$_2$NHCH$_2$CH$_2$—, or —CH$_2$CH$_2$OCH$_2$CH$_2$—; or R$_{11}$ and R$_{12}$ are taken together to form alkanediyl$_{(C≤6)}$;

or pharmaceutically acceptable salt thereof.

In particular combinations, R$_1$ is a substituent of formula (A), further G may be S, and further R$_4$, R$_5$ or R$_6$ may be hydrogen, including where R$_4$, R$_5$ and R$_6$ are each hydrogen.

In any of the preceding embodiments, R$_2$ may be hydrogen.

In any of the preceding embodiments, R$_3$ may be —NR$_{11}$R$_{12}$, including where R$_{12}$ or R$_{13}$ is cyclopropyl, cyclobutyl, cyclopentyl or cyclohexyl, and in particular where R$_{12}$ or R$_{13}$ is cyclopropyl.

The method may further employ a compound of formula (II):

(II)

wherein:

R$_{11}$ and R$_{12}$ are both hydrogen; or R$_{11}$ is hydrogen and R$_{12}$ is substituted or unsubstituted alkyl$_{(C≤10)}$, substituted or unsubstituted alkenyl$_{(C≤10)}$, substituted or unsubstituted alkynyl$_{(C≤10)}$, or benzyl; or R$_{11}$ and R$_{12}$ taken together are —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$NHCH$_2$CH$_2$—, or —CH$_2$CH$_2$OCH$_2$CH$_2$—;

R$_4$, R$_5$ and R$_6$ are each independently:

hydrogen, halo, hydroxy, cyano, nitro; or alkyl$_{(C≤10)}$, aryl$_{(C≤12)}$, aralkyl$_{(C≤15)}$, heteroaryl$_{(C≤12)}$, acyl$_{(C≤10)}$ or a substituted version of any of these groups; and G is O, NH, or S, or a pharmaceutically acceptable salt thereof. Where G is S, R$_4$, R$_5$ or R$_6$ may in particular be hydrogen, including where R$_4$, R$_5$ and R$_6$ are each hydrogen.

In any of the preceding embodiments, R$_{11}$ may be hydrogen.

In any of the preceding embodiments, R$_{12}$ may be cyclopropyl or an aliphatic$_{(C≤10)}$ alcohol or an aliphatic$_{(C≤10)}$ polyol.

A particular example of the compound is:

or a pharmaceutically acceptable salt thereof.

In any of the preceding embodiments, the cell is located in an animal subject. In any of the preceding embodiments, the cell is contacted ex vivo.

Also provided is compound having the formula:

Optionally formulated as a composition comprising the compound dispersed in a pharmaceutically-acceptable buffer, carrier, diluent or excipient.

The terms "contacted" and "exposed," when applied to a cell, are used herein to describe the process by which a compound of the invention is delivered to a target cell or is placed in direct juxtaposition with the target cell.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

FIGS. 1A-E. Isx (LSH-1) induces expression of insulin and transcription factors in primary cultured human islets. (FIG. 1A) Primary human islets that had been cultured in RPMI 160 for 6 months were treated with vehicle or 40 μM Isx for 1 or 2 d. Expression of human insulin and glucagon genes was assessed by Taqman quantitative RT-PCR. (FIG. 1B) Insulin secretion measured by ELISA over 24 h from islets treated with Isx or vehicle for 1 or 2 d. (FIG. 1C) Total insulin content of islets cultured for 3 mo and fresh islets, each treated for 48 h with Isx or DMSO. (FIG. 1D) Time course of pancreatic gene induction in islets cultured for 1 year treated with DMSO (8 days) or 40 μM Isx for 2, 4 or 8 days. (FIG. 1E) Immunohistochemical staining using antibodies against insulin, BETA2, Neurogenin3 (Ngn3) and MafA of islets cultured for 2 months and treated with Isx or vehicle for 48 h. Nuclei were stained with DAPI.

(FIG. 2A) Dose-response relationship of MIN6 cells treated with 5-80 μM Isx for 24 h or DMSO (0.08%–similar to the highest concentration of Isx). Whole cell lysates (40 μg) were subjected to immunoblotting using antibodies against BETA2/NeuroD1, MafA, PDX-1, pERK1/2 (pT183/pY185), acetylated histones ACH4-K5K8K12K16 and ACH3K9 and total histone H3. (FIG. 2B) Quantitative RT-PCR of murine insulin1 and insulin2 gene expression in MIN6 cells treated with Isx for 24 h as in FIG. 2A. (FIG. 2C) GSIS in 15 min from MIN6 cells pretreated with Isx or vehicle for 48 h in the presence or absence of the MEK1/2 inhibitor U0126 for 24 h. (FIG. 2D) Insulin content measured by ELISA in MIN6 cells treated with Isx for 24 or 48 h. (FIG. 2E) GSIS induced by glucose, amino acids (AA) and Exendin-4 (Ex-4) singly or in combination in MIN6 cells pretreated with Isx for 48 h.

(FIG. 3A) Insulin promoter reporter activity in HEK293 cells transfected with BETA2, MafA, PDX-1, or (FIG. 3B) WT MafA or mutant MafA, treated with Isx or vehicle for 24 h. (FIG. 3C) Immunoblotting of anti-myc immunoprecipates using anti-acetyl lysine (Ac-K) and anti-BETA2 from cells overexpressing myc-BETA2. (FIG. 3D) Chromatin immunoprecipitation (ChIP) analysis of MafA and BETA2 (FIG. 3E) association with the insulin promoter in MIN6 cells in response to a 10-min glucose stimulation.

FIGS. 4A-G. Isx (LSH-1) is a HAT activator. (FIG. 4A) Immunoblots of acetylated histones in MIN6 cells pretreated with the indicated inhibitors for 16 h and then treated with vehicle or Isx. (FIGS. 4B-C) HDAC (FIG. 4B) and HAT (FIG. 4C) activities in 50 μg of nuclear extract protein from MIN6 cells treated with Isx or DMSO for 24 h. Trichostatin A (TSA; 2 μM) was added at as a positive control. HeLa nuclear extract also was included as a positive control. (FIGS. 4D-E) HAT activity from nuclear extracts of MIN6 cells without (FIG. 4D) or with (FIG. 4E) expression of p300 for 48 h, pretreated with Isx or 10 μM U0126 for 24 h. (FIG. 4F) ChIP analysis of the association of p300 with the insulin gene promoter in MIN6 cells upon glucose (Gluc) stimulation after pretreatment with Isx and/or U0126 for 24 h. Statistical analysis was performed using Student's t test as in FIGS. 1A-E. *P<0.05; **P<0.01. (FIG. 4G) Simplified view of the actions of Isx.

(FIG. 5A) Structure of the lead compound N-cyclopropyl-5-(thiophen-2-yl)isoxazole-3-carboxamide (Isx) used in this study. (FIG. 5B) Expression profiles of relevant islet factors by Sybr-Green qPCR analyses from human islets cultured for 1 year as in FIG. 1D. (FIG. 5C) Insulin immunohistochemical staining in human islets cultured for 2 months. Nuclei are stained with DAPI. (FIG. 5D) Immunoblotting of whole cell extracts from human islets cultured for six months treated with vehicle (DMSO) or Isx for 24 h. (FIG. 5E) Human islets cultured for 6 months were treated with DMSO (Veh) or Isx for 48 h. To implicate signaling pathways that are required for the isoxazole-driven increase in β cell function, measured as GSIS, the isoxazole-treated islets were also treated with vehicle (Veh), 10 μM U0126 (U), 10 μM Nifedipine-BAPTA (N-B), or 0.1 μM wortmannin (W) for the duration of the isoxazole treatment.

(FIG. 7A) Beta2:myc, Pdx-1:myc and MafA:myc were transfected singly or in combination in HEK293 cells together with the rat Insulin 1 promoter (−410,+1) Luciferase reporter (pGL3-rIns). The basal activity of the promoter was assessed by transfection of the empty pcDNA vector alone. Transfected cells were treated with vehicle or 20 μM isoxazole for 24 h. sv40-Renilla luciferase was used as an internal control. (FIG. 7B) Expression of recombinant factors Beta2:myc, Pdx-1:myc and MafA:myc transfected in HEK293 cells as in (FIG. 7A), was determined by immunoblot using NeuroD1, PDX-1 and cMaf antibodies. (FIG. 7C) Expression profile of transfected WT and mutant MafA:myc in HEK 293 cells treated with vehicle or isoxazole for 24 h.

FIGS. 8A-D. Isx (LSH-1) stimulated HAT activity. (FIG. 8A) Combined effect of Isx treatment for 24 h and WT ERK2 (W) or kinase dead K52R ERK2 (R) on the HAT activities of p300, and (FIG. 8B) other HATs, CBP, PCAF and GCN5-L2, transfected in HEK293 cells. Specific effects of Isx on GSIS in MIN6 cells (FIG. 8C) and NRx2.5 promoter activity in P19 progenitor cells (FIG. 8D) compared to HDAC inhibitors such as Trichostatin A (TSA) or valproic acid (VPA) after pretreatment for 48 h.

(FIG. 14A) Acute treatment of MIN6 cells with 20 μM Isx derivatives induced rapid intracellular calcium influx compared to DMSO alone. (FIG. 14B) Insulin secretion measured by ELISA after acute stimulation with 20 μM Isx derivatives in the presence of 4 or 20 mM glucose or with 20 mM glucose plus 1× amino acids.

(FIG. 17A) Experimental design using MIN6 cells treated with BSA control or 1 mM FFA (Oleate: Palmitate 2:1 3 days, followed by treatment with 5 μM LSH-18 in the last day. Beta cell function is assessed by (FIG. 17A) glucose-induced ERK1/2 activation and (FIG. 17B) glucose-induced insulin secretion.

(FIG. 18A) Determination of gene expression profile by qPCR of human islets cultured for 2 months and treated with 10 μM Isx derivatives (LSH-1, LSH-18, LSH-18, LSH-20, LSH-49) for 7 days. (FIG. 18B) Determination of beta cell function by glucose-induced insulin secretion for 1 hr.

DESCRIPTION OF ILLUSTRATIVE EMBODIMENTS

Figure 2A:
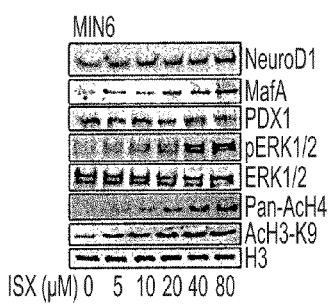
FIGS. 2A-E. Isx (LSH-1) activates insulin expression and improves β cell function in MIN6 cells.

The present invention overcomes the deficiencies of the prior art by providing compounds that induce insulin expression and secretion as well as treat diabetes. The inventors previously identified a family of 3,5-disubstituted isoxazole small molecules (Isx) by screening a chemical library in mouse pluripotent stem cells for activators of the gene encoding the homeodomain transcription factor NRx2.5 (Sadek et al., 2008). They discovered in collateral studies that Isx, although originally sought as a cardiogenic small molecule, had strong neurogenic activity in several types of neural progenitor cells (Schneider et al., 2008). This activity was mediated in part through chemical induction of BETA2/NeuroD1 expression. Due to the importance of BETA2 in the development of the pancreas and insulin production in pancreatic β cells, in this study the inventors examined effects of Isx on the properties of β cells. They find that this molecule increases insulin production and β cell function and restores insulin production by human islets following long term ex vivo culture. The also provide the initial characterization of the changes elicited by Isx to improve the essential behaviors of β cells. These, and other aspects of the invention, are set out in detail below.

A. Compounds of the Present Invention

Compounds of the present invention may be considered as derived from isoxazoles. The following compounds are representative of certain compounds of the present invention:

a compound of formula (I):

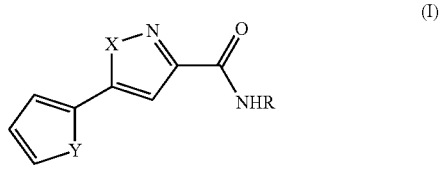

wherein X is O or NH, Y is S or O and R is H, a substituted or unsubstituted alkyl, such as $C_1$-$C_6$ alkyl or $C_3$-$C_6$ cycloalkyl, or a substituted or unsubstituted alkenyl, such as $C_2$-$C_6$ alkenyl, a substituted or unsubstituted alkynyl, such as $C_2$-$C_6$ alkynyl, or a stereoisomer, solvate, hydrate, or pharmaceutically acceptable salt thereof. In certain embodiments regarding compounds of formula (I), the proviso exists such that with the provisos that if X is O, then R must be a substituted or unsubstituted $C_3$-$C_6$ cycloalkyl; and/or if X is NH, then R must not be pyrazinyl substituted $C_1$-$C_6$ alkyl;

a compound of formula (Ia), (Ib), or (Ic):

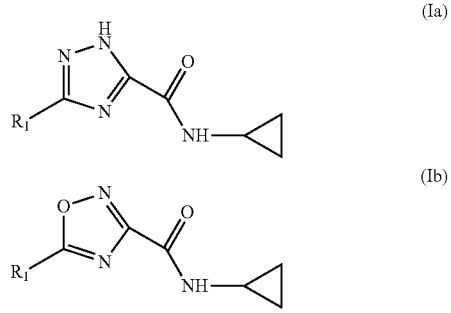

-continued

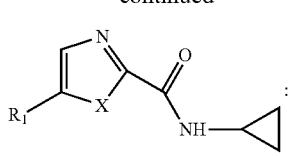

(Ic)

wherein $R_1$ is substituted or unsubstituted phenyl, unsubstituted pyrrolyl, unsubstituted pyridyl, unsubstituted furanyl, unsubstituted thienyl, unsubstituted benzofuranyl, unsubstituted benzo[b]thiophenyl, or unsubstituted thiazolyl. Any of these R1 substituents may be substituted as well;

a compound of formula (II):

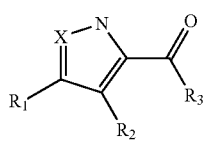

(II)

wherein: $R_1$ is substituted or unsubstituted phenyl, substituted or unsubstituted thiophenyl or a substituent of formula (A):

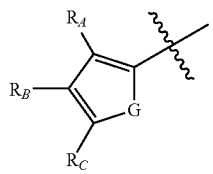

(A)

wherein: $R_A$, $R_B$ and $R_C$ are each independently selected from the group consisting of hydrogen, halogen, $C_1$-$C_6$ alkyl, $C_3$-$C_6$ cycloalkyl, aryl, cyano, nitro, and a carbonyl group; and G is O, —NH, or S; $R_2$ is hydrogen, hydroxy, halogen, nitro, aryl, alkyl, alkoxy, alkenyl, alkenyloxy, alkynyl, alkynyloxy, aralkyl, —CHO, —C(O)$R_9$, —OC(O)$R_9$, —OC(O)O$R_9$, —O(CN)O$R_9$, —C(O)N$R_9R_{10}$, —OC(O)N$R_9R_{10}$, —N$R_9$O$R_5$, or —SO$_3R_9$; wherein $R_9$ and $R_{10}$ are each independently hydrogen, alkyl, aryl, or aralkyl; $R_3$ is NH—O-alkyl, —NH—OH, —O$R_{11}$ or N$R_{11}R_{12}$, wherein $R_{11}$ and $R_{12}$ are each independently hydrogen, alkyl, alkenyl, alkynyl, aryl, or aralkyl; or $R_{11}$ and $R_{12}$ together form a cyclic group; or $R_{11}$ and $R_{12}$ together with the nitrogen to which they are bound form a cyclic group; X is O or —N$R_{13}$, wherein $R_{13}$ is hydrogen, alkyl, aryl, or aralkyl; or a stereoisomer, solvate, hydrate, or pharmaceutically acceptable salt thereof;

and a compound having formula (V):

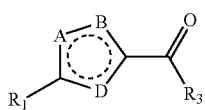

(V)

wherein: the ABD ring comprises two non-adjacent double bonds; A, B and D are each independently S, N, O, C, —N$R_{14}$, —C$R_{15}$, or —C$R_{15}R_{16}$, wherein $R_{14}$ is hydrogen, halogen, alkyl, aryl, or aralkyl; and $R_{15}$ and $R_{16}$ are each independently hydrogen, hydroxy, halogen, nitro, aryl, alkyl, alkoxy, alkenyl, alkenyloxy, alkynyl, alkynyloxy, aralkyl, —CHO, —C(O)$R_9$, —OC(O)$R_9$, —OC(O)O$R_9$, —O(CN)O$R_9$, —C(O)N$R_9R_{10}$, —OC(O)N$R_9R_{10}$, —N$R_9$O$R_5$, or —SO$_3R_9$; wherein $R_9$ and $R_{10}$ are each independently hydrogen, alkyl, aryl, or aralkyl, provided that at least two of A, B and D comprise S, N, or O; $R_1$ is alkyl, —CH=CH-aryl, or aryl; and $R_3$ is alkyl, aryl, aralkyl, —O$R_4$, or —N$R_4R_5$, wherein: $R_4$ and $R_5$ are each independently hydrogen, alkyl, aryl, or aralkyl; or $R_4$ and $R_5$ together form a cyclic group; or $R_4$ and $R_5$ together with the nitrogen to which they are bound form a cyclic group. In certain embodiments regarding compounds of formula (V), the proviso exists such that compounds of formula ($V_a$) are excluded:

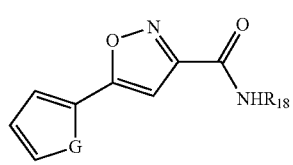

($V_a$)

wherein $R_{18}$ is alkyl, such as lower alkyl or cyclopentyl, or alkenyl, such as lower alkenyl or allyl, and G is O or S.

B. Chemical Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

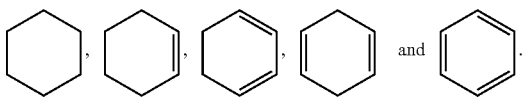

As will be understood by a person of skill in the art, no one such ring atom forms part of more than one double bond. The symbol " ⌇ ", when drawn perpendicularly across a bond indicates a point of attachment of the group. It is noted that the point of attachment is typically only identified in this manner for larger groups in order to assist the reader in rapidly and unambiguously identifying a point of attachment. The symbol " ◄▬ " means a single bond where the group attached to the thick end of the wedge is "out of the page." The symbol " ▬▬▬ " means a single bond where the group attached to the thick end of the wedge is "into the page". The symbol " ∿∿ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

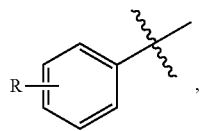

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

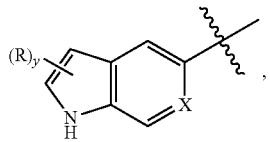

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals CH), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum number (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

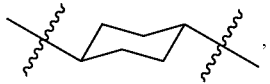 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups:

—CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

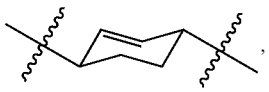 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

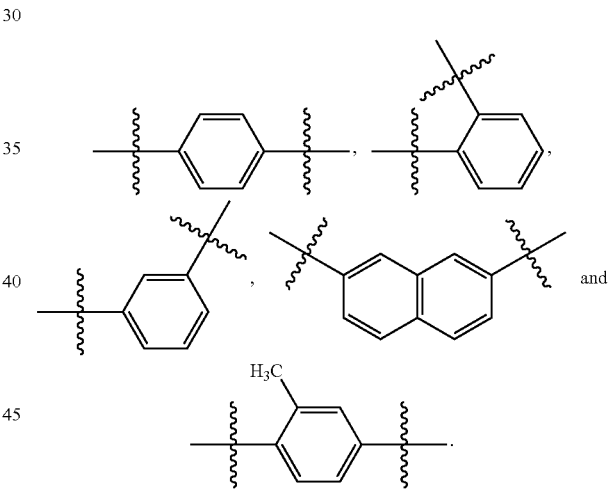

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group alkanediylaryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

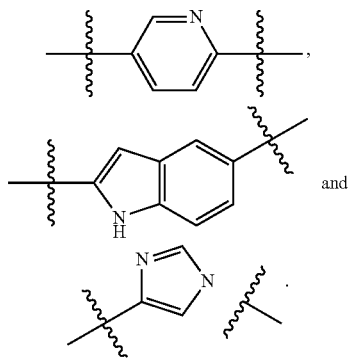

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃, —OCH₂CH₃, —OCH₂CH₂CH₃, —OCH(CH₃)₂, —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups —NHC(O)OCH₃ and —NHC(O)NHCH₃ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)₂, —OP(O)(OEt)(OMe) and —OP(O)(OEt)₂. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups S(O)$_2$R and S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (2002).

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. "Isoxazole derivatives," therefore, refers to a chemically modified compound that still retains the desired effects of the parent isoxazole prior to its chemical modification. Such effects may be enhanced (e.g., slightly more effective, twice as effective, etc.) or diminished (e.g., slightly less effective, 2-fold less effective, etc.) relative to the parent isoxazole, but may still be considered an isoxazole derivative. Such derivatives may have the addition, removal, or substitution of one or more chemical moieties on the parent molecule. Non-limiting examples of the types modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, Selection and Use (2002), which is incorporated herein by reference.

As used herein, the term "cyclic group" refers to a carbocycle group (e.g., cyclopropyl, cyclohexyl), a heterocycle group (e.g., pyrrolidinyl), an aryl group, or any combination thereof (e.g., fused bicyclic group).

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts (1999). Compounds of the present invention are specifically contemplated wherein one or more functional groups are protected by a protecting group.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers. For example, the following specific compounds contain asymmetric centers:

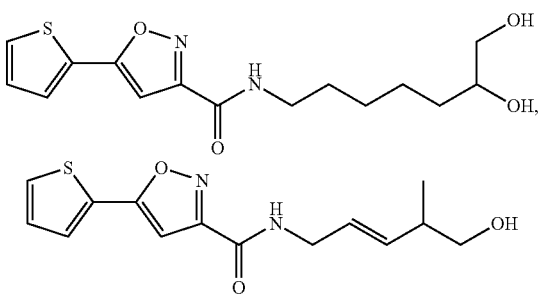

and are thus claimed as a racemic mixture (+/−), R (+) and S (−) forms.

Solvent choices for the synthetic preparation of compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In particular embodiments, purification is performed via silica gel column chromatography or HPLC.

In view of the above definitions, other chemical terms used throughout this application can be easily understood by those of skill in the art. Terms may be used alone or in any combination thereof. The preferred and more preferred chain lengths of the radicals apply to all such combination.

C. Diabetes and Insulin Deficiency

Diabetes mellitus, often simply referred to as diabetes, is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger).

There are three main types of diabetes:
- Type 1 diabetes: results from the body's failure to produce insulin, and presently requires the person to inject insulin. (Also referred to as insulin-dependent diabetes mellitus, IDDM for short, and juvenile diabetes.)
- Type 2 diabetes: results from insulin resistance, a condition in which cells fail to use insulin properly, and eventually combines with an absolute insulin deficiency. (Formerly referred to as non-insulin-dependent diabetes mellitus, NIDDM for short, and adult-onset diabetes.)
- Gestational diabetes: is when pregnant women, who have never had diabetes before, have a high blood glucose level during pregnancy. It may precede development of type 2 diabetes mellitus.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

All forms of diabetes have been treatable since insulin became available in 1921, and type 2 diabetes may be controlled with medications. Both type 1 and 2 are chronic conditions that usually cannot be cured. Pancreas transplants have been tried with limited success in type 1 diabetes; gastric bypass surgery has been successful in many with morbid obesity and type 2 diabetes. Gestational diabetes usually resolves after delivery. Diabetes without proper treatments can cause many complications. Acute complications include hypoglycemia, diabetic ketoacidosis, or nonketotic hyperosmolar coma. Serious long-term complications include cardiovascular disease, chronic renal failure, retinal damage. Adequate treatment of diabetes is thus important, as well as blood pressure control and lifestyle factors such as smoking cessation and maintaining a healthy body weight.

Diabetes is a huge health burden, costing an estimated $174 billion in 2007. In the United States alone more than 23 million people, ~8% of the population are diabetic; an additional 32% of adults are at risk with pre-diabetes, either impaired oral glucose tolerance or abnormally high fasting glucose (NIDDK, ADA statistics). This adds up to a staggeringly large proportion of the U.S. adult population with abnormal glucose metabolism. Worldwide, 230 million are affected by diabetes and the number is expected to double over the next 20 years. Currently, type 1 diabetes accounts for only 5% of the total. As obesity has become epidemic, type 2 diabetes has increased at an alarming rate. In spite of these daunting numbers, statistics also reveal that interventions that improve glycemic control reduce negative health consequences.

Most cases of diabetes mellitus fall into three broad categories: type 1, type 2, and gestational diabetes. A few other types are described. The term diabetes, without qualification, usually refers to diabetes mellitus. The rare disease diabetes insipidus has similar symptoms as diabetes mellitus, but without disturbances in the sugar metabolism.

The term "type 1 diabetes" has replaced several former terms, including childhood-onset diabetes, juvenile diabetes, and insulin-dependent diabetes mellitus (IDDM). Likewise, the term "type 2 diabetes" has replaced several former terms, including adult-onset diabetes, obesity-related diabetes, and non-insulin-dependent diabetes mellitus (NIDDM). Beyond these two types, there is no agreed-upon standard nomenclature. Various sources have defined "type 3 diabetes" as: gestational diabetes, insulin-resistant type 1 diabetes (or "double diabetes"), type 2 diabetes which has progressed to require injected insulin, and latent autoimmune diabetes of adults (or LADA or "type 1.5" diabetes).

Type 1 diabetes mellitus is characterized by loss of the insulin-producing beta cells of the islets of Langerhans in the pancreas leading to insulin deficiency. This type of diabetes can be further classified as immune-mediated or idiopathic. The majority of type 1 diabetes is of the immune-mediated nature, where β-cell loss is a T-cell mediated autoimmune attack. There is no known preventive measure against type 1 diabetes, which causes approximately 10% of diabetes mellitus cases in North America and Europe. Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

Type 2 diabetes mellitus is characterized by insulin resistance which may be combined with relatively reduced insulin secretion. The defective responsiveness of body tissues to insulin has an array of possible causes with obesity as a major factor. Diabetes mellitus occurrences linked to single gene mutations are known as maturity onset diabetes of the young or MODY and are classified separately. Type 2 diabetes is the most common type. In the early stage of type 2 diabetes, the predominant abnormality is reduced insulin sensitivity. At this stage hyperglycemia can be reversed by a variety of measures and medications that improve insulin sensitivity or reduce glucose production by the liver.

Gestational diabetes mellitus (GDM) resembles type 2 diabetes in several respects, involving a combination of relatively inadequate insulin secretion and responsiveness. It occurs in about 2%-5% of all pregnancies and may improve or disappear after delivery. Gestational diabetes is fully treatable but requires careful medical supervision throughout the pregnancy. About 20%-50% of affected women develop type 2 diabetes later in life. Even though it may be transient, untreated gestational diabetes can damage the health of the fetus or mother. Risks to the baby include macrosomia (high birth weight), congenital cardiac and central nervous system anomalies, and skeletal muscle malformations. Increased fetal insulin may inhibit fetal surfactant production and cause respiratory distress syndrome. Hyperbilirubinemia may result from red blood cell destruction. In severe cases, perinatal death may occur, most commonly as a result of poor placental perfusion due to vascular impairment. Labor induction may be indicated with decreased placental function. A cesarean section may be performed if there is marked fetal distress or an increased risk of injury associated with macrosomia, such as shoulder dystocia.

Some cases of diabetes are caused by the body's tissue receptors not responding to insulin (even when insulin levels are normal, which is what separates it from type 2 diabetes); this form is very uncommon. Genetic mutations (autosomal or mitochondrial) can lead to defects in beta cell function. Abnormal insulin action may also have been genetically determined in some cases. Any disease that causes extensive damage to the pancreas may lead to diabetes (for example, chronic pancreatitis and cystic fibrosis). Diseases associated with excessive secretion of insulin-antagonistic hormones can cause diabetes (which is typically resolved once the hormone excess is removed). Many drugs impair insulin secretion and some toxins damage pancreatic β-cells. The ICD-10 (1992) diagnostic entity, malnutrition-related diabetes mellitus (MRDM or MMDM, ICD-10 code E12), was deprecated by the World Health Organization when the current taxonomy was introduced in 1999.

D. Pharmaceutical Compositions and Methods of Treatment

1. Compositions

It is envisioned that, for administration to a host, compounds and cells of the present invention will be suspended in a formulation suitable for administration to a host. Aqueous compositions of the present invention comprise an effective amount of a compound and/or cells dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutically active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

2. Administration

Compounds and/or cells for administration will generally be formulated for parenteral administration, e.g., formulated for injection via the intravenous, intramuscular, subcutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration. Islet transplantation is particularly contemplated as part of the present invention.

Once transplanted, the islets begin to produce insulin, actively regulating the level of glucose in the blood. Islets are usually infused into the patient's liver. If the cells are not from a genetically identical donor, the patient's body will recognize them as foreign and the immune system will begin to attack them as with any transplant rejection. To prevent this, immunosupressant drugs are used. Recent studies have shown that islet transplantation has progressed to the point that 58% of the patients in one study were insulin independent one year after the operation.

The goal of islet transplantation is to infuse enough islets to control the blood glucose level removing the need for insulin injections. For an average-size person (70 kg), a typical transplant requires about one million islets, isolated from two donor pancreases. Because good control of blood glucose can slow or prevent the progression of complications associated with diabetes, such as nerve or eye damage, a successful transplant may reduce the risk of these complications. But a transplant recipient will need to take immunosuppressive drugs that stop the immune system from rejecting the transplanted islets.

Researchers use a mixture of highly purified enzymes called collagenases to isolate islets from the pancreas of a deceased donor. Collagenase solution is injected into the pancreatic duct which runs through the head, body and tail of the pancreas. Delivered this way, the enzyme solution causes distension of the pancreas, which is subsequently cut into small chunks and transferred into so-called Ricordi's chamber, where digestion takes place until the islets are liberated and removed from the solution. Isolated islets are then separated from the exocrine tissue and debris in a process called purification.

During the transplant, a radiologist uses ultrasound and radiography to guide placement of a catheter through the upper abdomen and into the portal vein of the liver. The islets are then infused through the catheter into the liver. The patient will receive a local anesthetic. If a patient cannot tolerate local anesthesia, the surgeon may use general anesthesia and do the transplant through a small incision. Possible risks of the procedure include bleeding or blood clots.

It takes time for the islets to attach to new blood vessels and begin releasing insulin. The doctor will order many tests to check blood glucose levels after the transplant, and insulin may be needed until control is achieved.

In particular, the Edmonton Protocol or a variation thereof is contemplated. The Edmonton Protocol is a method of implantation of pancreatic islets for the treatment of type 1 diabetes mellitus. The protocol involves isolating islets from a cadaveric donor pancreas using a mixture of enzymes called Liberase® (Roche). Each recipient receives islets from one to as many as three donors. The islets are infused into the patient's portal vein, followed by use of two immunosuppressants, sirolimus and tacrolimus, as well as the monoclonal antibody daclizumab, to prevent attack by the recipient's immune system. Sirolimus and tacrolimus, the two main drugs that keep the immune system from destroying the transplanted islets, must be taken for life.

Two of the most important limitations are the currently inadequate means for preventing islet rejection, and the limited supply of islets for transplantation. Current immunosuppressive regimens are capable of preventing islet failure for months to years, but the agents used in these treatments are expensive and may increase the risk for specific malignancies and opportunistic infections. In addition, and somewhat ironically, the most commonly used agents (like calcineurin inhibitors and rapamycin) are also known to impair normal islet function and/or insulin action. Further, like all medications, the agents have other associated toxicities, with side effects such as oral ulcers, peripheral edema, anemia, weight loss, hypertension, hyperlipidemia, diarrhea and fatigue. Perhaps of greatest concern to the patient and physician is the harmful effect of certain widely employed immunosuppressive agents on renal function. For the patient with diabetes, renal function is a crucial factor in determining long-term outcome, and calcineurin inhibitors (tacrolimus and ciclosporin) are significantly nephrotoxic. Thus, while some patients with a pancreas transplant tolerate the immunosuppressive agents well, and for such patients diabetic nephropathy can gradually improve, in other patients the net effect (decreased risk due to the improved blood glucose control, increased risk from the immunosuppressive agents) may worsen kidney function. Indeed, Ojo et al. have published an analysis indicating that among patients receiving other-than-kidney allografts, 7%-21% end up with renal failure as a result of the transplant and/or subsequent immunosuppression.

Like all transplantation therapies, islet transplantation is also handicapped by the limited donor pool. The numbers are striking; at least 1 million Americans have type 1 diabetes mellitus, and only a few thousand donor pancreata are available each year. To circumvent this organ shortage problem, researchers continue to look for ways to "grow" islets—or at least cells capable of physiologically regulated insulin secretion—in vitro, but currently only islets from cadaveric donors can be used to restore euglycemia. Further exacerbating the problem (and unlike kidney, liver, and heart transplants, where only one donor is needed for each recipient) most islet transplant patients require islets from two or more donors to achieve euglycemia. Lastly, the current methods for islet isolation need improvement, since only about half of attempted isolations produce transplant-ready islets. The present invention therefore provides improved methods for treating and stimulating β-cells, including those that have reduced insulin product or have lost the ability entirely. The compositions of the present invention and increase/reactivate the insulin production in these cells, and may further induce β-cell proliferation. The treatments may occur ex vivo following retrieval from a cadaver or the patient being treated, or following transplant in vivo.

Generally, dispersions are prepared by incorporating the compounds or cells into a sterile vehicle which contains the basic dispersion medium and the required other ingredients for maintaining cell viability as well as potentially additional components to effect proliferation, differentiation or replacement/grafting in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

3. Adjunct Therapies and Procedures

In accordance with the present invention, it may prove advantageous to combine the methods disclosed herein with adjunct therapies or procedures to enhance the overall anti-diabetic effect. Such therapies and procedures are set forth in general, below. A skilled physician will be apprised of the most appropriate fashion in which these therapies and procedures may be employed.

The present invention, though designed to eliminate the need for other therapies, is contemplated to provide advantageous use with traditional insulin supplementation, but at lower levels, such as below 90%, below 80%, below 70%, below 60%, below 50%, below 40%, below 30%, below 20%, below 15%, 10-15%, below 10%, 5-10%, below 5%, 4%, 3%, 2% or 1% of the normal daily dosage of insulin. Normal daily dosage for TD1 is 30-60 units per day. Such therapies should be tailored specifically for the individual patient given their current clinical situation, and it is contemplated that a subject could be "weaned" down or off insulin therapy after commencing isoxazole provision. The following are general guidelines for typical a "monotherapy" using insulin supplementation by injection, and can be applied here, albeit in the context of the aforementioned reductions in total daily dosage.

Insulin can be injected in the thighs, abdomen, upper arms or gluteal region. In children, the thighs or the abdomen are preferred. These offer a large area for frequent site rotation and are easily accessible for self-injection. Insulin injected in the abdomen is absorbed rapidly while from the thigh it is absorbed more slowly. Hence, patients should not switch from one area to the other at random. The abdomen should be used for the time of the day when a short interval between injection and meal is desired (usually pre-breakfast when the child may be in a hurry to go to school) and the thigh when the patient can wait 30 minutes after injection for his meal (usually pre-dinner). Within the selected area systematic site rotation must be practiced so that not more than one or two injections a month are given at any single spot. If site rotation is not practiced, fatty lumps known as lipohypertrophy may develop at frequently injected sites. These lumps are cosmetically unacceptable and, what is more important, insulin absorption from these regions is highly erratic.

Before injecting insulin, the selected site should be cleaned with alcohol. Injecting before the spirit evaporates can prove to be quite painful. The syringe is held like a pen in one hand, pinching up the skin between the thumb and index finger of the other hand, and inserting the needle through the skin at an angle of 45-90° to the surface. The piston is pushed down to inject insulin into the subcutaneous space (the space between the skin and muscle), then one waits for a few seconds after which release the pinched up skin before withdrawing the needle. The injection site should not be massaged.

For day-to-day management of diabetes, a combination of short acting and intermediate acting insulin is used. Some children in the first year after onset of diabetes may remain well controlled on a single injection of insulin each day. However, most diabetic children will require 2, 3 or even 4 shots of insulin a day for good control. A doctor should decide which regimen is best suited.

One Injection Regimen: A single injection comprising a mix of short acting and intermediate acting insulin (mixed in the same syringe) in 1:3 or 1:4 proportion is taken 20 to 30 minutes before breakfast. The usual total starting dose is 0.5 to 1.0 units/kg body weight per day. This regimen has three disadvantages: (1) all meals must be consumed at fixed times; (2) since the entire quantity of insulin is given at one time, a single large peak of insulin action is seen during the late and early evening hours making one prone to hyopglycemia at this time; (3) as the action of intermediate acting insulin rarely lasts beyond 16-18 hours, the patient's body remains under-insulinized during the early morning hours, the period during which insulin requirement in the body is actually the highest.

Two-Injection Regimen: This regimen is fairly popular. Two shots of insulin are taken—one before breakfast (⅔ of the total dose) and the other before dinner (⅓ of the total dose). Each is a combination of short acting and intermediate acting insulin in the ratio of 1:2 or 1:3 for the morning dose, and 1:2 or 1:1 for the evening dose. With this regimen the disadvantages of the single injection regimen are partly rectified. Some flexibility is possible for the evening meal. Further, as the total days' insulin is split, single large peaks of insulin action do not occur hence risk of hypoglycemia is reduced and one remains more or less evenly insulinized throughout the day. On this regimen, if the pre-breakfast blood glucose is high, while the 3 a.m. level is low, then the evening dose may need to be split so as to provide short acting insulin before dinner and intermediate acting insulin at bedtime.

Multi-Dose Insulin Regimens: The body normally produces insulin in a basal-bolus manner, i.e., there is a constant basal secretion unrelated to meal intake and superimposed on this there is bolus insulin release in response to each meal. Multi-dose insulin regimens were devised to mimic this physiological pattern of insulin production. Short acting insulin is taken before each major meal (breakfast, lunch and dinner) to provide "bolus insulin" and intermediate acting insulin is administered once or twice a day for "basal insulin." Usually bolus insulin comprises 60% of the total dose and basal insulin makes up the remaining 40%. With this regimen you have a lot of flexibility. Both the timing as well as the quantity of each meal can be altered as desired by making appropriate alterations in the bolus insulin doses. To take maximum advantage of this regimen, one should learn "carbohydrate counting" and work out carbohydrate:insulin ratio—the number of grams of carbohydrate for which the body needs 1 unit of insulin.

4. Monitoring Glucose Levels

Any person suffering from diabetes will be very familiar with the need to regularly measure blood glucose levels. Blood glucose level is the amount of glucose, or sugar, in the blood. It is also is referred to as "serum glucose level." Normally, blood glucose levels stay within fairly narrow limits throughout the day (4 to 8 mmol/l), but are often higher after meals and usually lowest in the morning. Unfortunately, when a person has diabetes, their blood glucose level sometimes moves outside these limits. Thus, much of a diabetic's challenge is to. When one suffers from diabetes, it is important that glucose level be as near normal as possible. Stable blood glucose significantly reduces the risk of developing late-stage diabetic complications, which start to appear 10 to 15 years after diagnosis with type 1 diabetes, and often less than 10 years after diagnosis with type 2 diabetes.

Blood glucose levels can be measured very simply and quickly with a home blood glucose level testing kit, consisting of a measuring device itself and a test strip. To check blood glucose level, a small amount of blood is placed on the test strip, which is then placed into the device. After about 30 seconds, the device displays the blood glucose level. The best way to take a blood sample is by pricking the finger with a lancet. Ideal values are (a) 4 to 7 mmol/l before meals, (b) less than 10 mmol/l one-and-a-half hours after meals; and (c) around 8 mmol/l at bedtime.

People who have type 1 diabetes should measure their blood glucose level once a day, either in the morning before breakfast or at bedtime. In addition, a 24-hour profile should be performed a couple of times a week (measuring blood glucose levels before each meal and before bed). People who have type 2 diabetes and are being treated with insulin should also follow the schedule above. People who have type 2 diabetes and who are being treated with tablets or a special diet should measure their blood glucose levels once or twice a week, either before meals or one-and-a-half hours after a meal. They should also perform a 24-hour profile once or twice a month.

The main advantage for measuring blood glucose levels of insulin-treated diabetics in the morning is that adjusted amounts of insulin can be taken if the blood glucose level is high or low, thereby reducing the risk of developing late-stage diabetic complications. Similarly, the blood glucose level at bedtime should be between 7 and 10 mmol/l. If blood glucose is very low or very high at bedtime, there may be a need to adjust food intake or insulin dose. Blood glucose should also be measured any time the patient does not feel well, or think blood glucose is either too high or too low. People who have type 1 diabetes with a high level of glucose in their blood (more than 20 mmol/l), in addition to sugar traces in the urine, should check for ketone bodies in their urine, using a urine strip. If ketone bodies are present, it is a warning signal that they either have, or may develop, diabetic acidosis.

E. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Figure 5A:
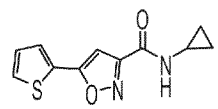
FIGS. 5A-E. Gene expression induced by Isx (LSH-1) in human islet cultures.
Figure 5C:
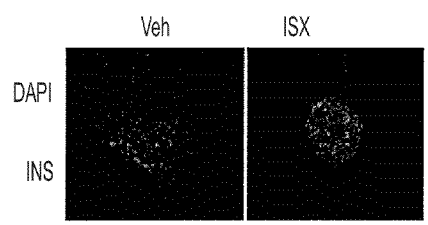

Materials. Antibodies against ERK1/2 and pERK1/2 were as described (Lawrence et al., 2008). The BETA2 (N-19), cMaf (M-153), PDX-1 (N-18) and p300 (C-20) antibodies were from Santa Cruz Biotechnology. Antibodies recognizing chromatin modifications, pan-ACH4 K5K8K12K16 (06-866), ACH3K9 (07-352), ACH3K14 (07-353), ACH3K9K14 (07-353), were from Upstate/Millipore Inhibitors were obtained from the following sources: U0126 and FK506-LC Laboratories; PD0325901-Stemgent; nifedipine and BAPTA-Calbiochem; wortmannin and trichostatin A-Sigma. The small molecule 3.5-disubstituted Isx was described previously and is shown in FIG. 5A (Sadek et al., 2008; Schneider et al., 2008).

Cell Culture and Treatments. MIN6 cells were cultured in DMEM (Gibco), containing 25 mM glucose, 10% fetal bovine serum, 10 mM Hepes pH 7.4, 10.2 mM L-glutamine, 50 mM sodium pyruvate, 2.5 mM β-mercaptoethanol, 100 U/ml penicillin and 100 µg/ml streptomycin at 37° C. in 10% $CO_2$. Human islets were obtained from the ICR Basic Science Islet Distribution and from the University of Alabama, Birmingham Islet Resource Facility and were cultured in RPMI 1640 with 11 mM glucose for up to 1 year. The medium was changed twice weekly and the islets were subcultured when they reached 90% confluence. For Isx treatments, cells were incubated in medium containing either Isx or the equivalent volume of DMSO vehicle (0.04%). To measure GSIS, cells were placed in Krebs-Ringer bicarbonate/Hepes containing 0.1% bovine serum albumin and 2 mM glucose for 2 h, and stimulated for 15 min with 20 mM glucose, a 1× amino-acid mixture (concentrations as in DMEM), or 50 nM Exendin-4. U0126 (10 µM), nifedipine (3 µM), BAPTA (10 µM), wortmanin (0.5 µM) or FK506 (0.1 µM) were added for 1-24 h as indicated.

DNA Constructs. The rat insulin 1 promoter-luciferase reporter construct (pGL3-rIns −410, +1) was described previously (Lawrence et al., 2005). Expression vectors encoding MafA:myc, PDX-1:myc and BETA2:myc were from Michael German (UCSF). p300 was a gift from Joseph Garcia (Southwestern). The MafA:myc point mutants were generated by Quik-Change mutagenesis (Agilent Technologies).

ChIP and Q-PCR Analyses. ChIP was as described (Lawrence et al., 2008) with the following modifications. Chromatin was cross-linked with 1% formaldehyde and sonicated with a Bioruptor 200 (Diagenode) in an ice cold water bath. Antibodies immobilized on protein A-Sepharose beads were used for immunoprecipitation. ChIP products were analyzed by real-time Q-PCR as previously described for real-time PCR analysis (Lawrence et al., 2008) using the following primers (5'-CAGACCTAGCACCAGGG-3' (SEQ ID NO:1) and 5'-GGACTTTGCTGTTTGTCCC-3' (SEQ ID NO:2)) to amplify the −157/−50 fragment of the mouse insulin promoter encompassing the C1 (MafA), E1 (BETA2) and A1 (PDX-1) binding sites. The results were expressed relative to input and presented as mean+/−SEM of at least two independent experiments in triplicate.

HAT and HDAC Assays. The histone acetyl transferase and deacetylase activities were measured in 50 µg of nuclear protein using the HAT and HDAC activity colorimetric assay kits from Biovision Biotechnology according to manufacturer's recommendations.

Gene Expression Analysis. Total RNA was extracted from human islet preparations with TRI reagent according to manufacturer's protocol (Ambion). cDNA was prepared from total RNA by a mixture of random hexamer- and oligo-dT-primed reverse transcription (iScript Biorad). The expression of insulin and glucagon relative to 18S RNA was evaluated by TaqMan assays (Applied Biosystems). Relative expression of pancreatic factors was determined using Power SYBR Green PCR Master Mix (Applied Bio systems). Primer sequences for qRT-PCR are in STable 1. SYBR Green and TaqMan probe-based PCR was performed using the ABI 7500 DNA Sequence Detection System with standard fluorescent chemistries and thermal cycling conditions specified by the manufacturer: 50° C. for 2 min, 95° C. for 10 min for one cycle and an additional 40 cycles at 95° C. for 15 sec, and then 58° C. for 1 min.

Luciferase Reporter Gene Assays. HEK 293 cells (0.15× $10^6$ cells) in triplicate were transfected with the pGL3-rIns reporter construct (0.1 µg/well) (Stratagene) and cotransfected with 0.5 µg/well of either empty vector (pcDNA3.1) or vectors encoding BETA2:myc, MafA:myc or PDX-1:myc using Lipofectamine 2000 (Invitrogen). After 24 h, cells were stimulated with 20 µM Isx or DMSO for another 24 h. Luciferase activity was measured using the dual luciferase reporter system (Promega) with Renilla Luciferase as an internal control.

Statistics. Experiments with two groups were analyzed for statistical significance using unpaired two-tailed Student's t-test. Error bars represent standard deviation (s.d.), unless otherwise stated. Values of $p<0.05$ were considered statistically significant.

Example 2

Results

Isx Increases Glucose-Induced Insulin Secretion and Enhances Expression of Factors Important for Insulin Gene Transcription in Human Islets. The inventors examined the effect of Isx on the function of β cells within human islets maintained in culture for up to one year. Based on concentration effects in cultured cells described below and earlier studies in other cell types (Sadek et al., 2008; Schneider et al., 2008), the majority of studies employed 20 or 40 µM Isx. In addition to β cells, islets contain two other major cell types, the α and δ cells which secrete glucagon and somatostatin, as well as γ or pp cells which secrete pancreatic polypeptide (Steiner et al., 2010). These cell types express both shared and cell-specific transcription factors mediating their distinct nutrient-regulated hormone secretions, and the interplay among them is important for islet function. After months in culture, islets display reduced expression of β-cell restricted transcription factors and become less able to secrete insulin in response to a glucose challenge (Buitrago et al., 1975; Hollande et al., 1976).

Treatment of human islets that had been in culture for 6 months with Isx for 1-2 days induced a large increase in preproinsulin mRNA, while glucagon mRNA decreased by nearly 80% under the same circumstances (FIG. 1A). Insulin secreted over a 24-h period from these islets was also markedly increased (FIG. 1B). To determine the relative significance of these changes caused by the compound, we compared effects of Isx on human islets cultured for three months to newly obtained human islets. Insulin content in the 3 month-old islets was increased 10-fold by Isx, to a value nearly 75% of the insulin content of islets isolated only 1 week earlier (FIG. 1C). In addition, a 2-day exposure to Isx increased the insulin content of the fresh islets by close to 25%. Islets in culture for 2 months and treated with Isx for 2 days revealed an obvious increase in Ngn3, BETA2, and insulin immunostaining (FIG. 1E).

Figure 5B:
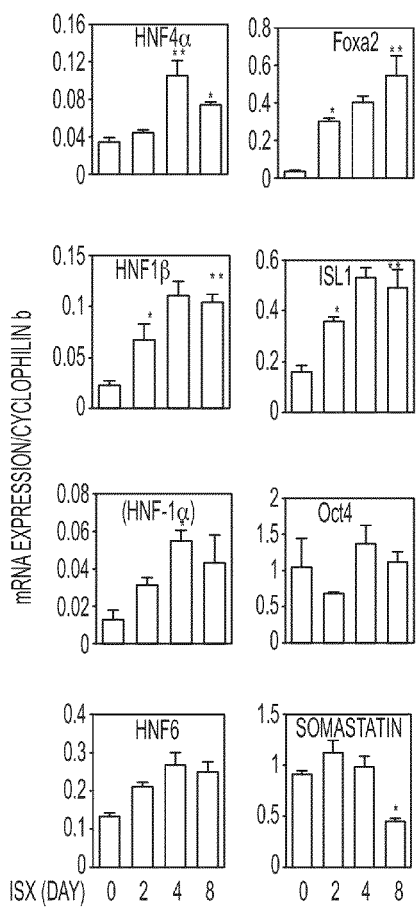
Figure 5D:
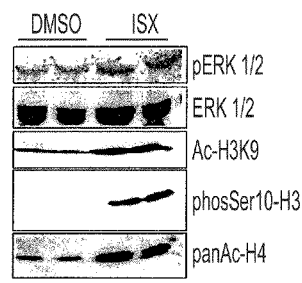

The inventors examined a time course of Isx action on a series of mRNAs in islets maintained in culture for one year. Preproinsulin mRNA was increased by 10-fold at 24 h and by 50-fold or more after several days of Isx exposure (FIG. 1D). Because Isx also increased glucose-responsiveness, the inventors assessed its effects on the expression of glucokinase and Glut2, proteins essential to the glucosesensing characteristics of β cells, and found that both increased markedly, peaking after 4 days of exposure. Along with BETA2, the inventors examined expression of transcription factors associated with insulin gene transcription as well as differentiation and differentiated functions of β cells. The majority of those tested displayed one of two expression patterns temporally. Several increased throughout the time course or increased until reaching a plateau; in addition to insulin itself, these included BETA2, MafA, PDX-1, Pax6, NRx6.1, NRx2.2, Foxa2, Hnf6, Hnf1α, Hnf1β, Hnf4α, and Is11 (Wilson et al., 2003; Lyttle et al., 2008; Oliver-Krasinski and Stoffers, 2008; Scearce et al., 2002; White et al., 2008) (FIG. 1D and FIG. 5B). Others which increased rapidly and then decreased with longer times of exposure included Ngn3 and Pax4. Increases in PDX-1, the Hnfs, and Is11 were relatively small, while increases in the other factors were generally more than 10-fold. Neither PCNA, an indicator of proliferation, nor Oct4, a factor associated with stem cells, showed consistent or substantial changes in mRNA expression.

Isx Increases Expression of BETA2 and Insulin Secretion from MIN6 β Cells.

Figure 2B:
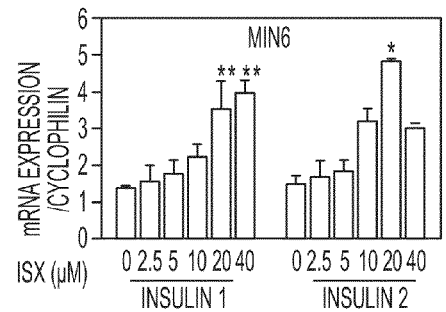
Figure 6:
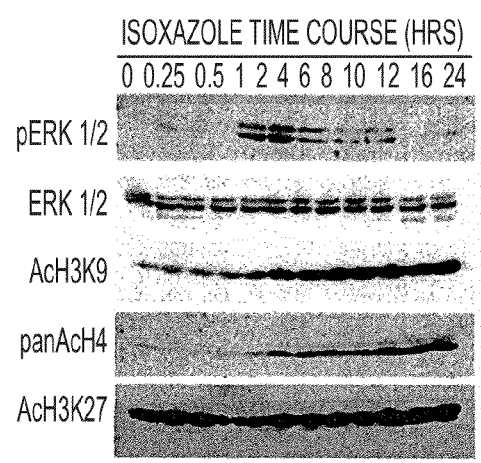
FIG. 6. Time course of Isx (LSH-1) treatment in MIN6 cells. Immunoblotting of whole cell extracts from MIN6 cells grown for 24 h in complete DMEM containing 4.5 mM glucose and treated with 20 μM Isx for from 15 min to 24 h. The control (0 min) was treated with DMSO for 24 h.

To examine changes induced by Isx in isolated MIN6 β cells, the inventors first showed that Isx enhanced expression of BETA2 and other factors in this cultured β cell line. After 24 h of exposure, immunoreactive BETA2 increased at all concentrations of Isx tested (FIG. 2A). MafA expression also increased substantially, while there was little if any change in PDX-1 detected. The inventors then examined activities of ERK1/2, which are essential for glucose-stimulated insulin gene transcription. Isx-enhanced ERK1/2 phosphorylation was detectable following 24 h of exposure. A time course of treatment with 20 μM Isx indicated a biphasic effect on ERK1/2 with a small initial activation within the first few minutes, followed by a slower, more pronounced and sustained activation beginning around 2 h of Isx exposure (FIG. 6). Acetylation of histone H3 and H4, indicators of gene induction, were also increased by Isx in β cells, as was found previously in other cell types treated with this compound (Sadek et al., 2008). All of these changes were accompanied by as much as a 4-fold increase in preproinsulin mRNA (FIG. 2B).

Figure 2C:
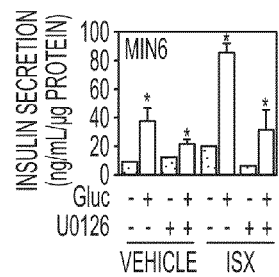
Figure 2D:
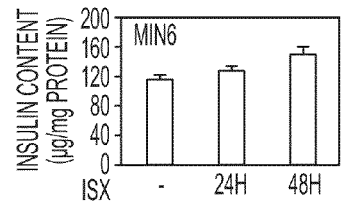
Figure 2E:
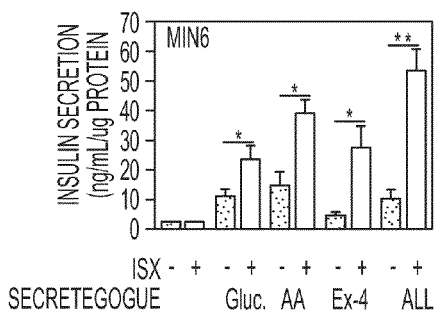
Figure 5E:
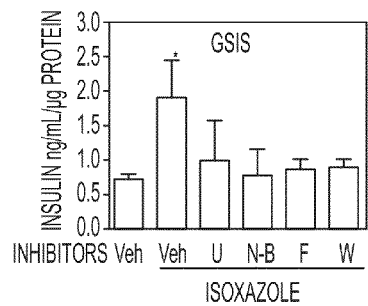

To examine insulin secretion, MIN6 β cells were incubated in complete medium with 4.5 mM glucose for 24 h prior to treatment with Isx. Glucose-stimulated insulin secretion (GSIS) was increased nearly 4-fold by Isx pretreatment (FIG. 2C), in spite of a relatively small increase in insulin content (FIG. 2D). The increase in GSIS was partially blocked by inhibiting ERK1/2 activation using a MEK inhibitor. Follow-up experiments showed that Isx increased stimulation of insulin secretion by glucose, amino acids and exendin-4 (a long acting glucagon-like peptide 1 agonist), individually and in combination from 2 to 5-fold (FIG. 2E). Effects of other inhibitors on Isx-enhanced GSIS were also explored. The calcineurin inhibitor FK506, which also inhibits ERK1/2 (Lawrence et al., 2005), the PI 3-kinase inhibitor wortmannin, and nifedipine, an inhibitor of L-type voltage-dependent calcium channels, together with the chelator BAPTA, all reduced the increase in GSIS caused by Isx (FIG. 5E).

Figure 3A:
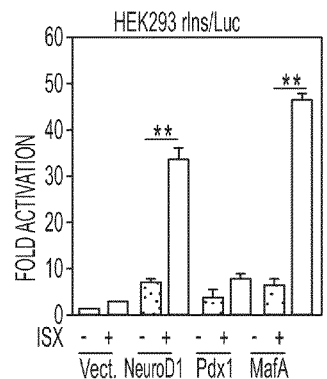
FIGS. 3A-E. Isx (LSH-1) activates transcription factors that regulate insulin gene expression and insulin production.
Figure 3B:
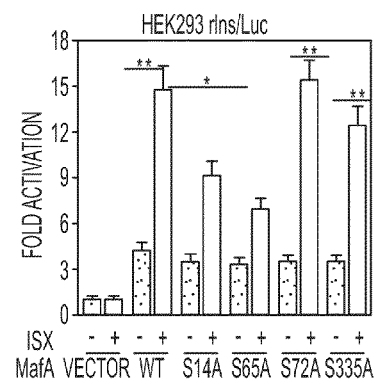
Figure 3C:
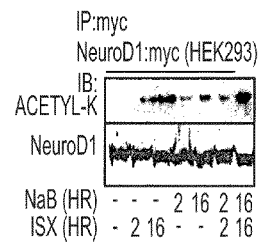
Figure 3D:
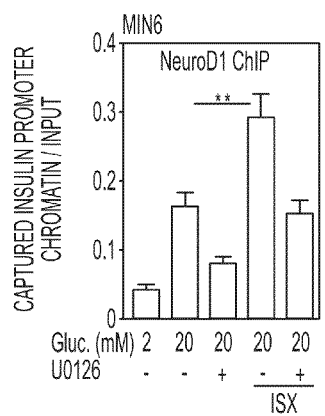
Figure 3E:
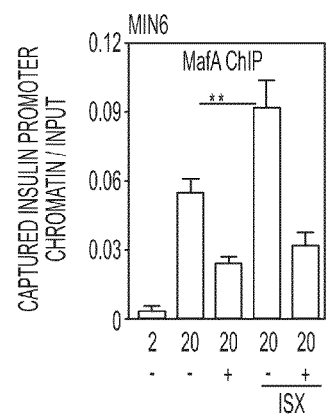
Figure 7A:
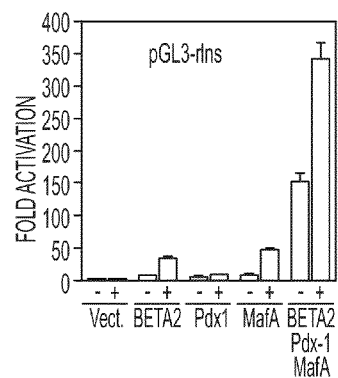
FIGS. 7A-C. Transient transfections and insulin reporter assays in HEK293 cells.
Figure 7B:
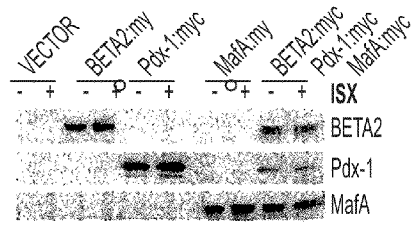
Figure 7C:
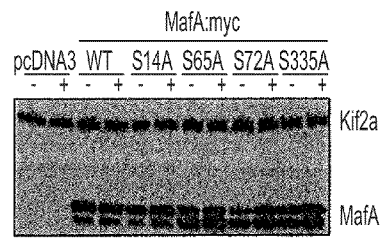

Epigenetic Mechanisms Contributing to Isx Action. To explore functional changes caused by Isx, we used overexpression and reconstitution assays in MIN6 and 293 cells to determine if the activities of factors that were induced were also impacted by the compound. Insulin gene reporter activity was increased by 4-fold or more by either BETA2 or MafA in the presence of Isx (FIG. 3A, FIG. 7). In contrast, the activity of PDX-1 was increased by two-fold or less by Isx. Comparable or greater chromatin binding of BETA2 and MafA to the insulin gene promoter was caused by Isx; Isx-induced binding was inhibited by blocking activation of ERK1/2 (FIGS. 3D-E), as was shown previously for glucose-stimulated binding of these factors (Lawrence et al., 2005). Isx also caused acetylation of BETA2 more strongly than the HDAC inhibitor sodium butyrate (FIG. 3C). Although BETA2 is an ERK1/2 substrate (Khoo et al., 2003), we have been unable to show that MafA is an ERK1/2 substrate. MafA regulatory phosphorylation on serine-proline sites by other enzymes has been reported (Benkhelifa et al., 2001; Han et al., 2007). Consistent with a role for serine modification, mutation of serine 65 and to a lesser extent serine 14 limited the ability of Isx to enhance MafA transcriptional activity (FIG. 3B).

Isx Regulates Histone Acetylation by Enhancing HAT Activity. Previously we showed that Isx decreased phosphorylation of HDAC5 and enhanced its nuclear export, possibly accounting for changes in transcription of NRx2.5 (Schneider et al., 2008). Here we find that, in addition to an effect on acetylation of BETA2, Isx also had a marked effect on acetylation of histones (FIG. 4A). Nifedipine, a calcium channel blocker, in combination with the chelating agent BAPTA, decreased acetylation of H3 on lysines 9 and 14 induced by Isx, but had little effect on acetylation of H4. The MEK/ERK pathway inhibitors U0126 and PD325901 inhibited Isx-induced acetylation of H4, as did the calcineurin inhibitor FK506, but had little effect on H3 acetylation. In contrast, the PI-3 kinase inhibitor wortmannin had no effect on either of these readouts.

To determine the basis for increased histone acetylation in β cells, HDAC and HAT activities were measured in nuclear extracts from MIN6 or HeLa cells treated with vehicle or Isx for 24 h (FIGS. 4B-C). HDAC activity in MIN6 cells was not affected by the compound, although it was inhibited by the HDAC inhibitor trichostatin A (Bieliauskas and Pflum, 2008). Units of activity were similar in MIN6 and HeLa nuclear extracts. On the other hand, HAT activity in nuclear extracts from Isx-treated MIN6 cells was increased ~2-fold by Isx. HAT activity in the Isx-treated cells was partially dependent on ERK1/2, as suggested by MEK inhibitor sensitivity (FIG. 4D). Effects of Isx on HATs expressed in 293 cells indicated that p300 and CBP, but not PCAF or GCN5, activities were increased by a combination of ERK2 expression and Isx, but blocked by expression of kinase-dead ERK2 (K52R) (FIG. 8). To validate the apparent regulation of p300 by Isx, p300 was expressed in MIN6 cells. Isx increased HAT activity in the nuclear extracts over and above that from expressed p300; U0126 inhibited the Isx-induced increase in HAT activity. Chromatin recruitment of p300 to the insulin promoter upon stimulation by glucose was increased by Isx pretreatment in an ERK1/2-dependent manner (FIG. 4E). These findings are consistent with the conclusion that Isx stimulates p300 activity and that Isx-induced changes in histone and transcription factor acetylation are caused at least in part by regulation of p300.

Reporter Assay Using the Rat Insulin Reporter Activity in MIN6 (Beta Cells Line).

Figure 9:
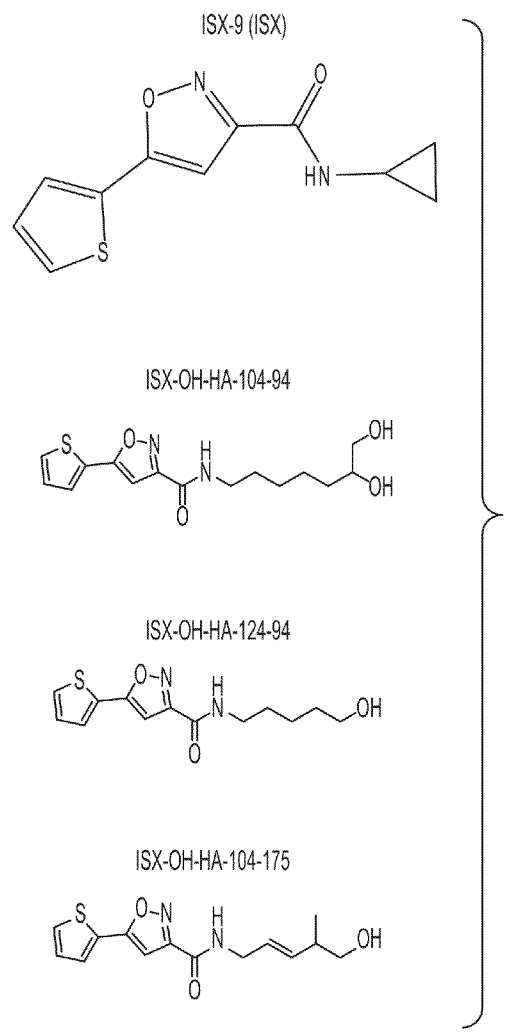
FIG. 9. Isoxazole compound structures.
Figure 10:
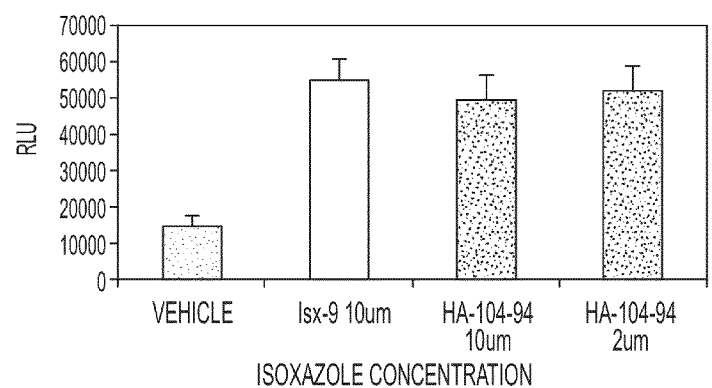
FIG. 10. Reporter assay using the rat insulin reporter activity in MIN6 (beta cell line).
Figure 11:
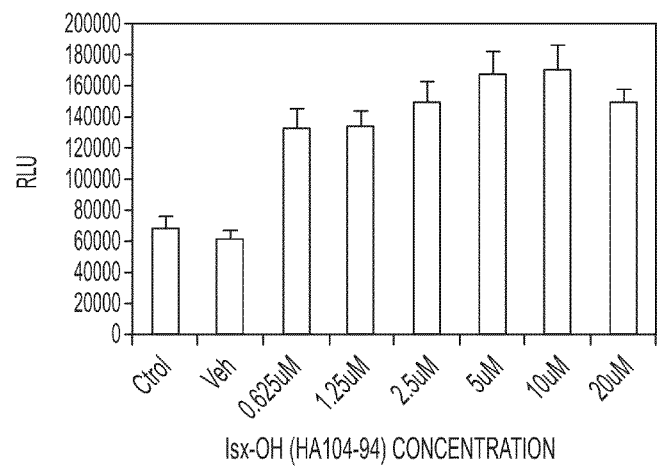
FIG. 11. Dose-response assay using the rat insulin reporter activity in MIN6.

Additional isoxazole compounds are shown in FIG. 9 (Isx-9 I the same as Isx discussed above). In a first experiment, Isx-9 treatment (10 µM) was compared to that of HA-104-94 (10 µM and 2 µM). Even at 2 µM, the HA-104-94 molecule had activity comparable to Isx-9 at 10 µM (FIG. 10). Next, the inventors found that concentrations as low as 0.625 µM of HA-104-94 can activate the insulin gene reporter 2-fold (FIG. 11).

Figure 12:
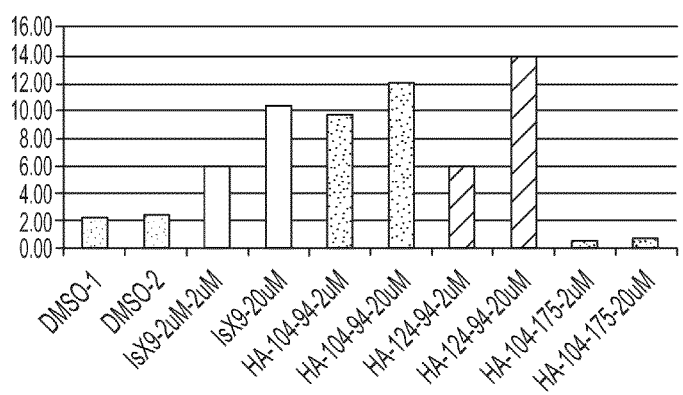
FIG. 12. Induction of endogenous insulin expression in MIN6 cells with Isx compounds.

Expression of Endogenous Insulin in MIN6 Cells. Isx-9 activates the endogenous insulin gene expression optimally at 20 µM concentration. In comparison to related small molecules at 2 µM and 20 µM, the Isx-OH (HA-104-94) has a larger capacity to turn on the insulin gene a 2 µM, similar to Isx-9 at 20 µM (FIG. 12).

Figure 13:
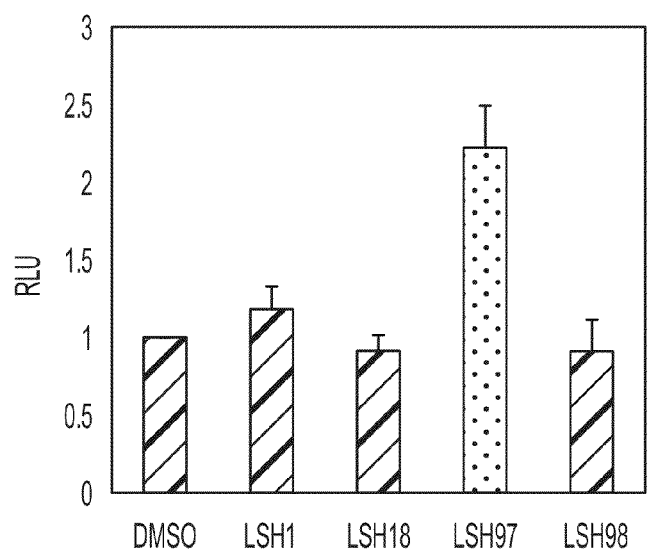
FIG. 13. Insulin promoter reporter assay. Insulin promoter luciferase reporter was transfected in MIN6 cells treated with various isoxazole molecules or DMSO (vehicle) for 24 hrs.
Figure 19:
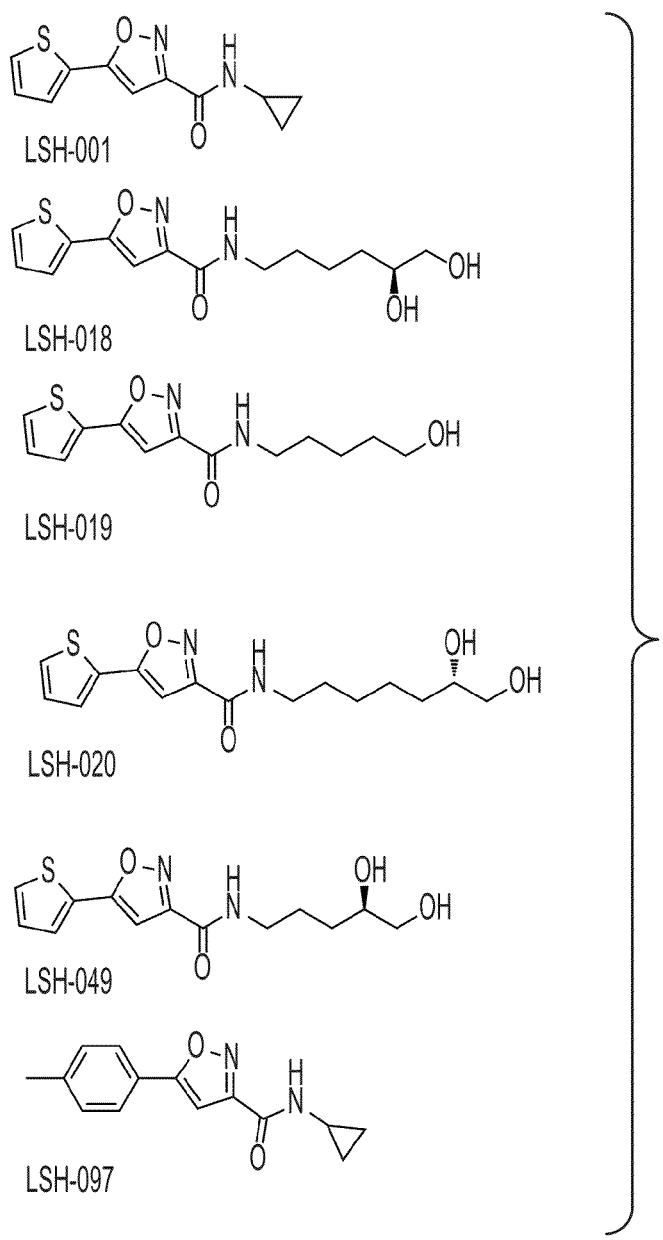
FIG. 19. Structures of Isoxazole molecules.

Identification of New Isoxazole Compounds. Based on a structure activity relationship (SAR) screen, the inventors characterized properties of several isoxazole-related compounds (FIG. 19). Two were selected (LSH-18 and LSH-97) for more detailed analysis because they performed better than the parental isoxazole molecule LSH1, of the present invention, at submicromolar concentrations in enhancing beta cell function and insulin secretion. As shown in FIG. 13, LSH-97 is still effective at 62.5 nM.

Figure 14A:
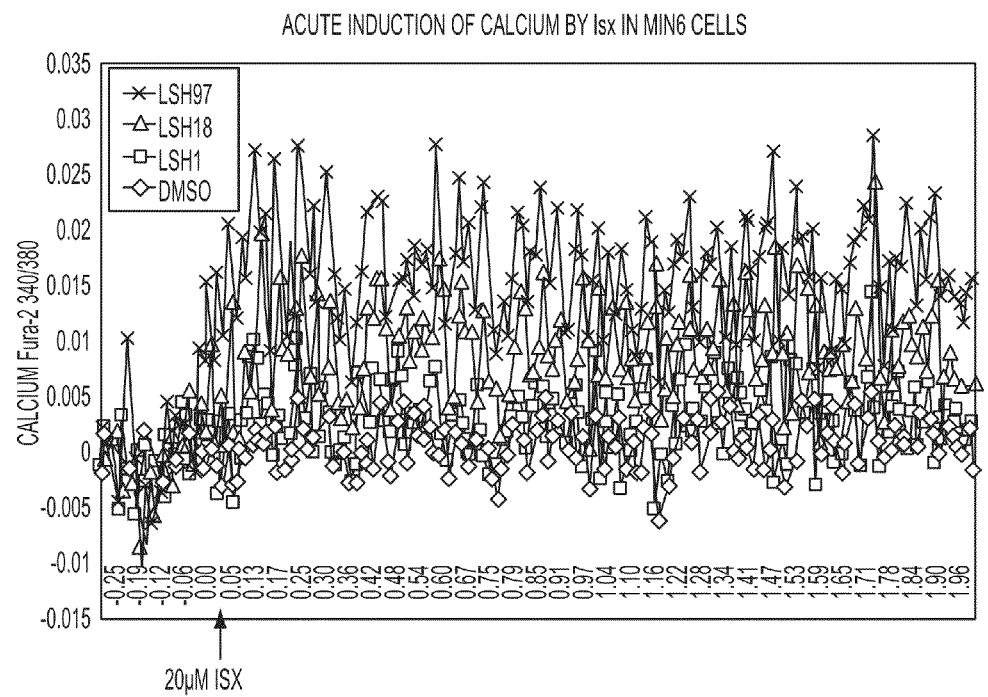
FIGS. 14A-B.
Figure 14B:
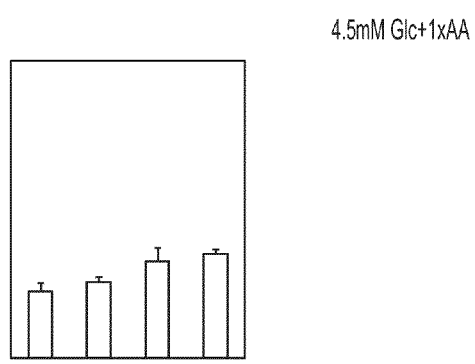

2-ISX Compounds Enhance Insulin Secretion in Response to Glucose and Receptor-Activated Secretagogues. It is important to recognize that the isoxazole derivatives discussed here are not insulin secretagogues because they do not induce insulin secretion upon treatment. Instead, the Isx molecules enhance pancreatic beta cell function. Pretreated beta cells showed significantly greater insulin secretion in response to stimulation with glucose, amino acids (AA) or Exendin-4 (Ex-4) a GLP1-receptor agonist (FIG. 14).

Figure 15A:
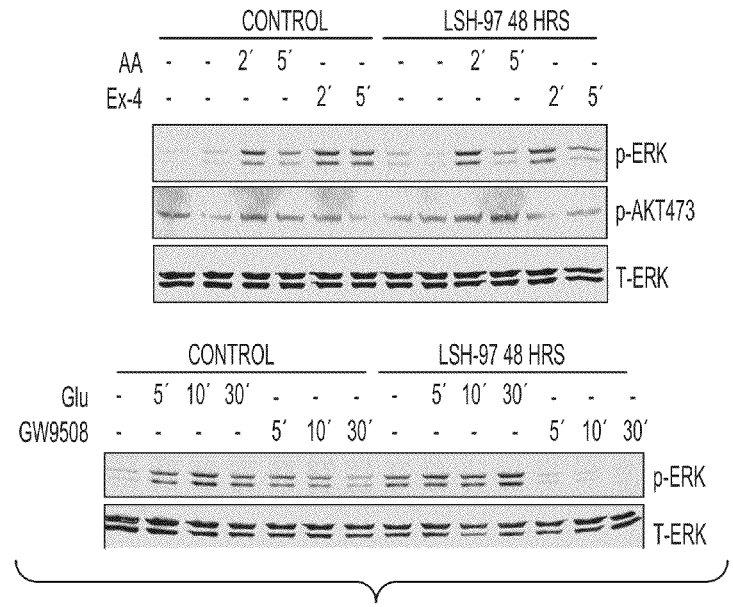
FIGS. 15A-B. Signaling (FIG. 15A) and insulin secretion after 30 minutes (FIG. 15B) in response to several secretagogues in MIN6 cells pretreated with 1 μM LSH-097 for 48 hrs.
Figure 15B:
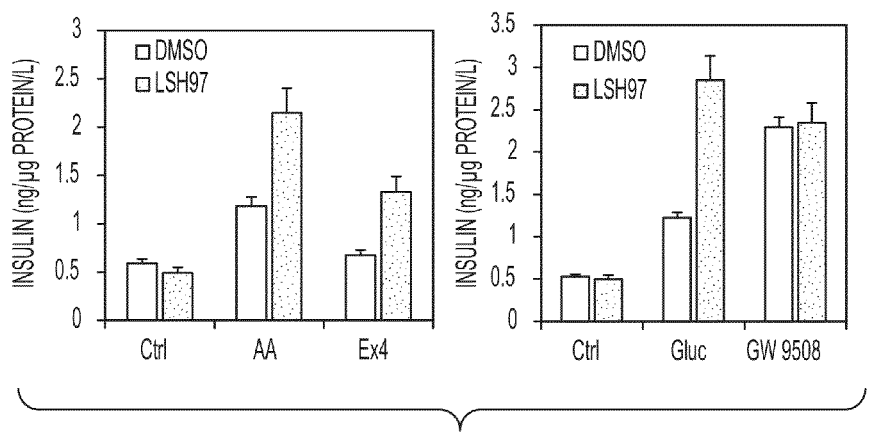

Pretreatment with 1 µM LSH-097 Enhances Beta Cell Function. The Isx molecules have the capacity to induce epigenetic changes (histone acetylation) that activate gene expression. The Isx molecules likely improve terminal differentiation of the beta cells, thus enhancing their function. For example, FIG. 15A shows A-Signaling after stimulation by amino acids (AA), Exendin-4 (Ex-4), glucose or the GPR40 (fatty acid receptor 1) agonist GW9508 with or without pretreatment with 1 µM LSH-97 for 48 hr. FIG. 15B shows Insulin secretion in MIN6 cells pretreated with 1 µM Isx LSH-97 for 48 hrs.

The Isx derivative LSH-097 (and LSH-18, data not shown) improves beta cell function and can be used to potentiate glucose-dependent insulin secretion, although it does not induce substantial secretion alone. LSH-097 enhances insulin secretion selectively in the presence of stimulatory concentrations of glucose, amino acids, and GLP1, (and probably others) but not by ligands for GPR40.

Figure 16A:
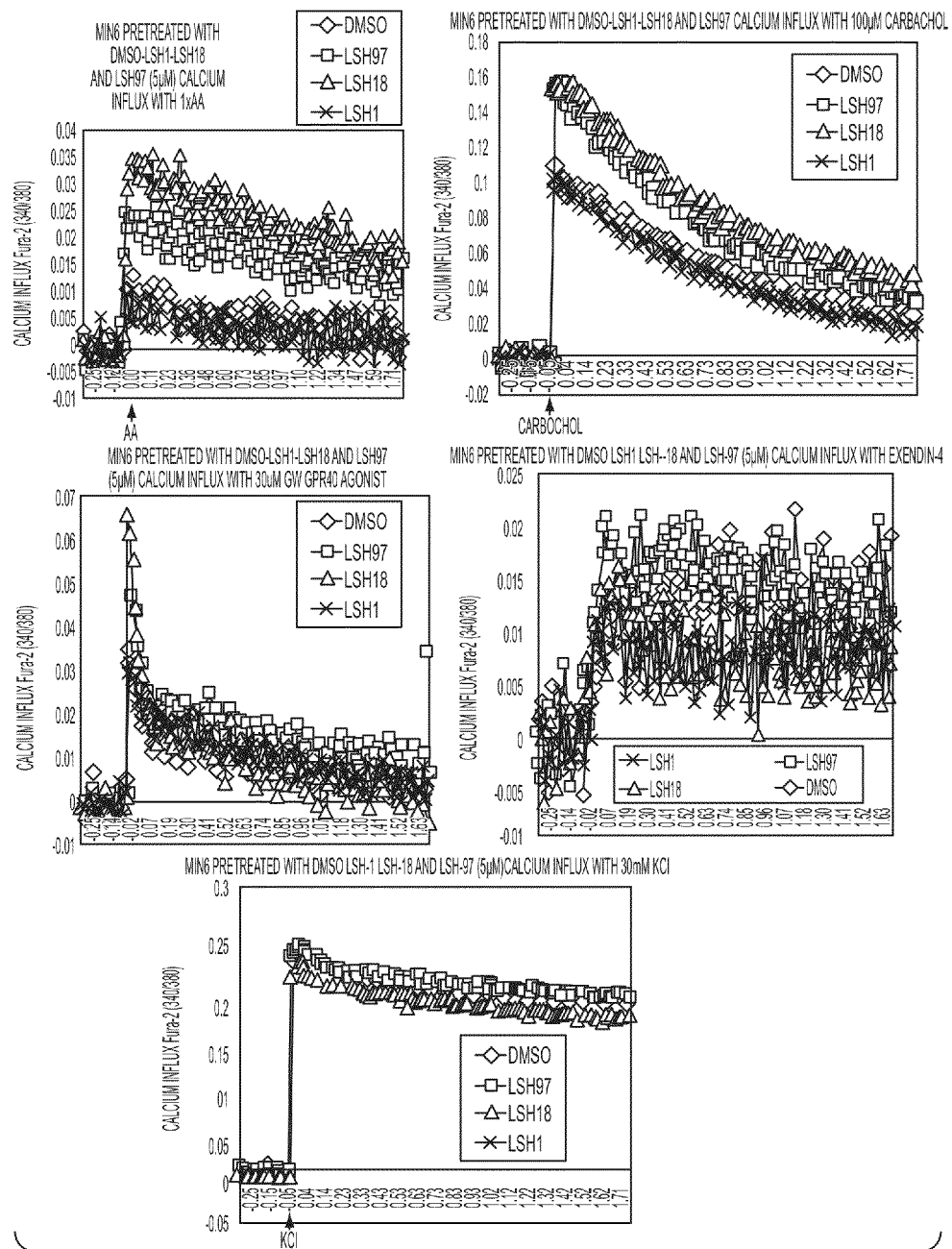
FIGS. 16A-B. Intracellular calcium influx in MIN6 cells pretreated with DMSO (vehicle) or 5 μM Isx derivatives LSH-001, LSH-018 and LSH-097 for 30 hrs (FIG. 16A) by ratiometric Fura-2 fluorescence. The peak of calcium influx after stimulation with the respective secretagogues (FIG. 16B).
Figure 16B:
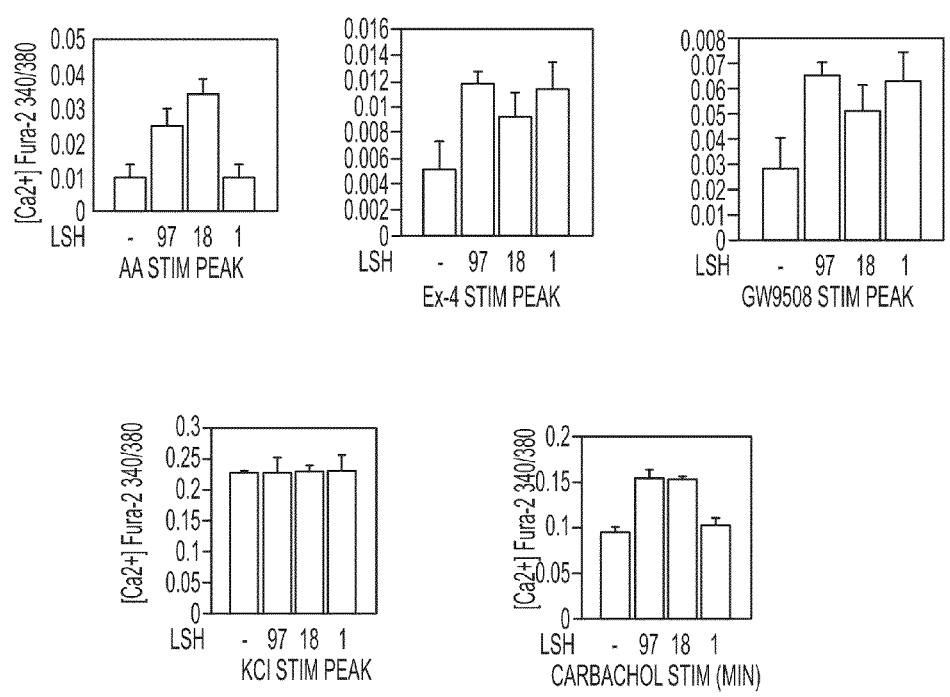

Calcium Influx as a Method to Measure Beta Cell Function. The rise in intracellular calcium triggers regulated insulin secretion in beta cells. In MIN6 cells, the improvement in insulin secretion is accompanied by a significant stimulation of intracellular calcium influx induced by secretagogues (FIGS. 16A-B).

Figure 17A:
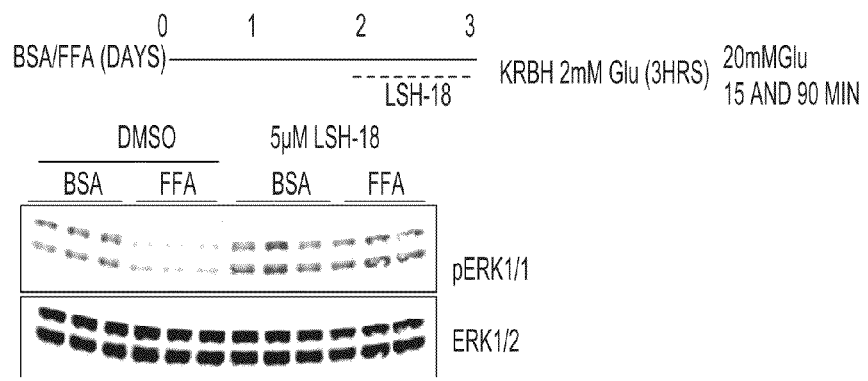
FIGS. 17A-B.
Figure 17B:
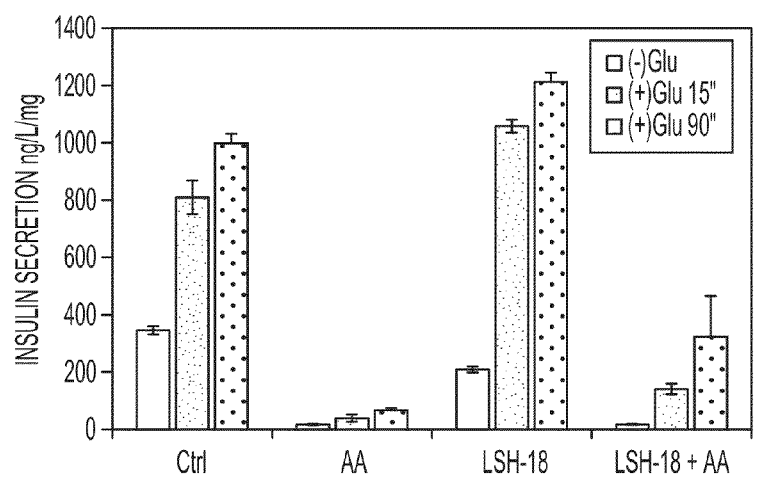

Isoxazoles Protect Pancreatic Beta Cells from Free Fatty Acid (FFA) Induced Dysfunction. LSH-018 and LSH-097 significantly improved insulin secretion in response to various secretagogues except GW9508. In fact, LSH-018 (FIGS. 17A-B) and LSH-097 (data not shown) significantly reduced MAP kinase ERK1/2 signaling induced by the free fatty acid receptor GPR40 agonist without having any effect on its amplifying effect on insulin secretion.

GPR40 and GPR120 are necessary for fatty acid (FFA) induction of ER stress and gluco-lipotoxicity which is a major cause of beta cell loss in type II diabetes. FFA can potentiate glucose-induced insulin secretion in the short term, however long term exposure to FFA has a detrimental effect and impairs beta cell function, reminiscent of type II diabetes progression. The inventors thus hypothesize that isoxazole small molecules may prevent loss of beta cell function and apoptosis during lipotoxic insult.

Figure 18A:
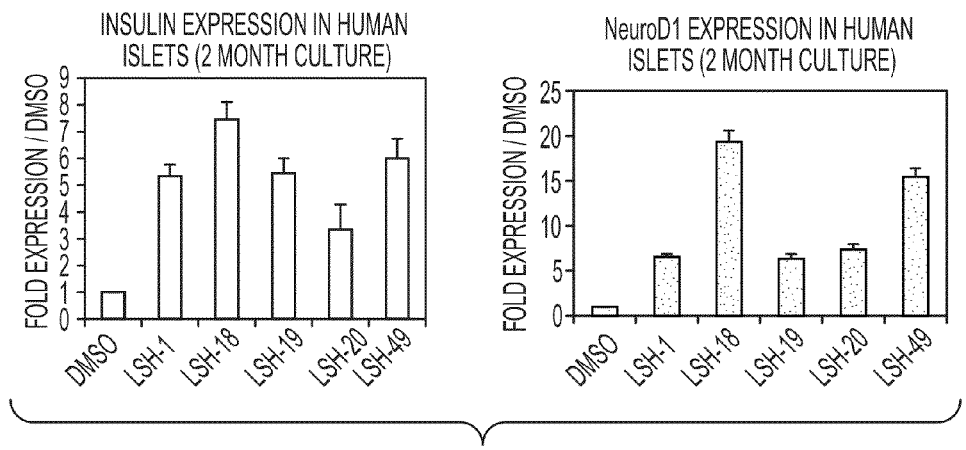
FIGS. 18A-B. Gene expression profile.
Figure 18B:
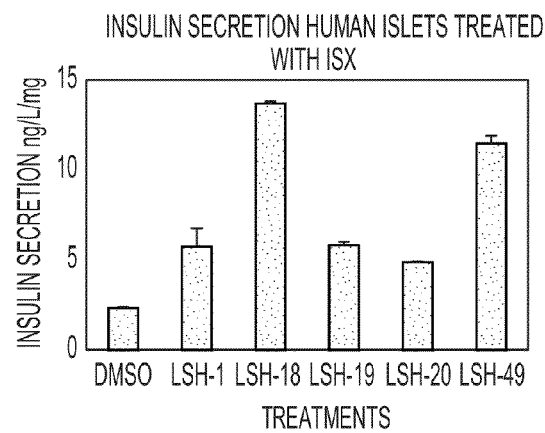

Effects of Isx in Cultured Human Islets. When put in culture long enough, human pancreatic islets lose the expression of islet factors, which will correlate with loss of glucose induced insulin secretion. In order to determine whether the new Isx compounds can perform better that the parental LSH-1, human islets cultured for 2 months were treated with various LSH compounds for 7 days results can be replicated in cultured human islets. Several Isx molecules significantly increased insulin synthesis as measured by increased transcript levels (FIG. 18A) and protein levels (FIG. 18B).

Example 3

Discussion

Isx increased the expression of transcription factors, including MafA and BETA2, that enhance β cell differentiation and control nutrient-responsive insulin gene transcription, resulting in an increase in preproinsulin mRNA and intracellular insulin content. Isx potentiated insulin secretion induced by nutrient and hormonal secretagogues prior to the increase in intracellular insulin content, indicating that it also adjusts the efficiency of the secretory machinery. The end result is a substantial increase in characteristics essential for mature β cell function, insulin biosynthesis and release in response to secretory challenge.

To create these changes in culture-aged islets, Isx induced a phalanx of factors that direct β-cell differentiation. These transcription factors have functions, often overlapping, in β-cell development and several have overlapping functions in mature 0 cells as well (Oliver-Krasinski and Stoffers, 2008). Ngn3 induces BETA2 expression in pancreatic precursors and suppresses cell division through induction of a cyclin-dependent kinase inhibitor (Miyatsuka et al., 2011). Ngn3 arises early in islet differentiation prior to the distinction between α and β cells and, in contrast to some of the other factors, Ngn3 becomes undetectable in the adult pancreas (Huang et al., 2000; Schwitzgebel et al., 2000). BETA2 and Ngn3, although not functionally redundant, can both drive islet differentiation and induce the homeodomain protein NRx2.2 (White et al., 2008; Gasa et al., 2008; Gu et al., 2010); Ngn3 also induces Pax4. NRx2.2 and Pax4 are required for development of the β-cell lineage (Habener and Stoffers, 1998; Smith et al., 2000; Smith et al., 2003; Brun and Gauthier, 2008).

Along with Foxa2 and PDX-1, NRx2.2 directly regulates MafA expression (Anderson et al., 2009; Doyle and Sussel, 2007; Raum et al., 2006; Lynn et al., 2007). NRx6.1, also downstream of NRx2.2, is required for the development of β-cell precursors specifically during the secondary wave of β-cell development (Sander et al., 2000). NRx6.1 also suppresses glucagon expression, perhaps accounting for repression of glucagon by Isx. In addition to its developmental roles, Foxa2 is also important in glucose metabolism and insulin secretion, regulating genes including the ATP-sensitive K+ channel subunits, Kir6.2 and Sur-1 (Wang et al., 2002; Lee et al., 2002; Lantz et al., 2004; Gao et al., 2007). Maturity onset diabetes of the young (MODY) can be caused by mutations in Hnf4α, Hnf1α, and Hnf1β, which also regulate a number of molecules important for glucose-sensing and other β-cell functions (Eeckhoute et al., 2001; Gupta et al., 2005). Among MafA targets are glucokinase, Glut2, the glucagon-like peptide 1 receptor, and prohormone convertase (Pcsk1) which processes proinsulin (Wang et al., 2007). Consistent with the control of these genes by MafA, its overexpression caused a left shift in glucose sensitivity of insulin secretion (Wang et al., 2007). Induction of these proteins by MafA is likely to contribute to enhanced insulin production and the improved secretory responsiveness of β cells and islets exposed to Isx.

Isx stimulated acetylation of nuclear proteins, through an action on acetyltransferases including p300. p300 has a major impact on differentiation and differentiated functions of β cells including transcription of the insulin gene (Sharma et al., 1999; Qiu et al., 1998). In addition to modification of histones, p300 can acetylate other proteins that support β cell function, for example BETA2 (Qiu et al., 2004). Studies with mutants suggest that acetylation of BETA2 affects both DNA binding and activation functions. Recently, mutations in the Kruppel-like factor KLF11 (MODY 7) revealed an association with early-onset type 2 diabetes (Neve et al., 2005). KLF11 is activated by p300 as are a large fraction of other MODY genes (Fernandez-Zapico et al., 2009).

Thus, activation of p300 is likely to be one of the significant mechanisms of Isx action. Signaling events regulated by Isx include biphasic activation of ERK1/2 that is temporally distinct from that induced by nutrients. Several glucose-sensitive insulin gene transcription factors are regulated by ERK1/2. Although MafA does not seem to be a physiological ERK1/2 substrate, chromatin binding of MafA along with BETA2 and PDX-1 is ERK1/2-dependent (Lawrence et al., 2005; Lawrence et al., 2008). ERK1/2 also phosphorylate p300 and control its activity and chromatin association, perhaps explaining the partial suppression of Isx-enhanced p300 activity caused by U0126 or coexpression of the kinasedead ERK2 mutant (Chen et al., 2007; Foulds et al., 2004). Loss of p300 from the insulin gene promoter is accompanied by loss of these three essential factors, suggesting that an ERK1/2-regulated event is acetylation which is thought to control access of the three factors to the proximal promoter.

Several strategies have been described to generate beta cells from stem cells, pancreatic duct, and other differentiated cell types (Borowiak and Melton, 2009). The majority of these involved the heterologous expression of groups of transcription factors or staged groups of hormonal factors that induce beta cell differentiation (Kobinger et al., 2005; Zhang et al., 2009; D'Amour et al., 2006; Zhou et al., 2008; Kroon et al., 2008). A small molecule was identified that induced pancreatic progenitors from embryonic stem cells (Chen et al., 2009). Compounds that enhanced β cell proliferation have also been reported (Wang et al., 2009). The plant alkaloid, conophylline, can induce beta cell differentiation from rat pancreatic acinar cells and fetal pancreatic tissue following 3-6 weeks of treatment (Kawakami et al., 2010). In addition to its apparently slower time course of action, conophylline increases the expression of PDX-1 mRNA to a greater extent than was noted here for Isx, suggesting distinct mechanisms of action.

In conclusion, Isx is among relatively few single molecules identified thus far that can dramatically improve beta cell function. Isx derivatives are new tools to study β-cell function and leads for drugs capable of rescuing insulin biosynthesis in dormant human islets prior to transplantation and perhaps directly in diabetic patients. The compounds currently available are unlikely to be useful in patients because they require micromolar concentrations to exert their effects. Nevertheless, they are valuable aids to develop noninvasive approaches to improve β-cell function.

Several isoxazole small molecules discussed here induce the expression of factors relevant for pancreatic beta cell homeostasis and function. Therefore, these and other isoxazole derivatives may be useful as agents for the prophylaxis or treatment of diabetes. Use of isoxazole compounds should be associated with a low risk of induction of hypoglycemia, which can be a negative consequence associated with insulin secretagogues such as receptor agonists and sulfonylureas. It is possible that they may also have beneficial effects on the inhibitory consequences of high fatty acid diets.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson et al., *BMC. Dev. Biol.*, 9:65, 2009.
Aramata et al., *Biochim. Biophys. Acta*, 1730:41-46, 2005.
Benkhelifa, et al., *Mol. Cell. Biol.*, 21:4441-4452, 2001.
Bieliauskas and Pflum, *Chem. Soc. Rev.*, 37:1402-1413, 2008.
Borowiak and Melton, *Curr. Opin. Cell Biol.*, 21:727-732, 2009.
Brun and Gauthier, *J. Mol. Endocrinol.*, 40:37-45, 2008.
Buitrago et al., *Diabetologia*, 11:535-540, 1975.
Bundgaard, *Drugs of the Future*, 16:443-458, 1991.
Bundgaard, In: *Design of Prodrugs*, 7-9; 21-24, Elsevier, Amsterdam, 1985.

Chae et al., *Mol. Cells*, 18:271-288, 2004.
Chen et al., *J. Biol. Chem.*, 282:27215-27228, 2007.
Chen et al., *Nat. Chem. Biol.*, 5:258-265, 2009.
D'Amour et al., *Nat. Biotechnol.*, 24:1392-1401, 2006.
Doyle and Sussel, *Diabetes*, 56:1999-2007, 2007.
Eeckhoute et al., *Mol. Endocrinol.*, 15:1200-1210, 2001.
Fernandez-Zapico et al., *J. Biol. Chem.*, 284:36482-36490, 2009.
Foulds et al., *Mol. Cell. Biol.*, 24:10954-10964, 2004.
Gao et al., *Cell Metab.*, 6:267-279, 2007.
Gasa et al., *Differentiation*, 76:381-391, 2008.
Gasa et al., *Proc. Natl. Acad. Sci. USA*, 101:13245-13250, 2004.
Genuth et al., *Diabetes Care*, 26:3160-3167, 2003.
Goodge and Hutton, *Cell Dev. Biol.*, 11:235-242, 2000.
Greene and Wuts, In: *Protecting Groups in Organic Synthesis*, 3$^{rd}$ ed., John Wiley & Sons, Inc., 1999.
Gu et al., *Cell Metab.*, 11:298-310, 2010.
Gupta et al., *J. Clin. Invest.*, 115:1006-1015, 2005.
Habener and Stoffers, *Proc. Assoc. Am. Physicians*, 110:12-21, 1998.
Halban et al., *J. Clin. Endocrinol. Metab.*, 95:1034-1043, 2010.
Han et al., *Mol. Cell. Biol.*, 27:6593-6605, 2007.
*Handbook of Pharmaceutical Salts: Properties, Selection and Use*, Stahl and Wermuth (Eds.), Verlag Helvetica Chimica Acta, 2002.
Hollande et al., *J. Physiol.* (Paris), 72:815-832, 1976.
Huang et al., *Mol. Cell. Biol.*, 20:3292-3307, 2000.
Kageyama et al., Int. *J. Biochem. Cell Biol.*, 29:1389-1399, 1997.
Kawakami et al., *Biomed. Pharmacother.*, 64:226-231, 2010.
Khoo et al., *J. Biol. Chem.*, 278:32969-32977, 2003.
Kobinger et al., *Mol. Ther.*, 11:105-111, 2005.
Kroon et al., *Nat. Biotechnol.*, 26:443-452, 2008.
Lantz et al., *J. Clin. Invest.*, 114:512-520, 2004.
Lawrence et al., *J. Biol. Chem.*, 280:26751-26759, 2005.
Lawrence et al., *Proc. Natl. Acad. Sci. USA*, 105:13315-13320, 2008.
Lee et al., *Diabetes*, 51:2546-2551, 2002.
Lynn et al., *Proc. Natl. Acad. Sci. USA*, 104:10500-10505, 2007.
Lyttle et al., *Diabetologia*, 51:1169-1180, 2008.
Miyatsuka et al., *Proc. Natl. Acad. Sci. USA*, 108:185-190, 2011.
Muoio and Newgard, *Nat. Rev. Mol. Cell. Biol.*, 9:193-205, 2008.
Neve et al., *Proc. Natl. Acad. Sci. USA*, 102:4807-4812, 2005.
Newgard and McGarry, *Annu. Rev. Biochem.*, 64:689-719, 1995.
Ohneda et al., *Semin. Cell Dev. Biol.*, 11:227-233, 2000.
Oliver-Krasinski and Stoffers, *Genes Dev.*, 22:1998-2021, 2008.
Qiu et al., *J. Biol. Chem.*, 279:9796-9802, 2004.
Qiu et al., *Mol. Cell. Biol.*, 18:2957-2964, 1998.
Raum et al., *Mol. Cell. Biol.*, 26:5735-5743, 2006.
Redmon et al., *Diabetes*, 43:546-551, 1994.
Rutter and Parton, Front Horm. Res., 36:118-134, 2008.
Sadek et al., *Proc. Natl. Acad. Sci. USA*, 105:6063-6068, 2008.
Sander et al., *Development*, 127:5533-5540, 2000.
Scearce et al., *Diabetes*, 51:1997-2004, 2002.
Schneider et al., *Nat. Chem. Biol.*, 4:408-410, 2008.
Schwitzgebel et al., *Development*, 127:3533-3542, 2000.
Sharma et al., *Mol. Cell. Biol.*, 19:704-713, 1999.
Smith et al., *J. Biol. Chem.*, 275:36910-36919, 2000.
Smith et al., *J. Biol. Chem.*, 278:38254-38259, 2003.
Sommer et al., *Mol. Cell. Neurosci.*, 8:221-241, 1996.
Steiner et al., *Diabetes Obes. Metab.*, 11(Suppl 4):189-196, 2009.
Steiner et al., *Islets.*, 2:135-145, 2010.
Vaxillaire and Froguel, *Endocr. Rev.*, 29:254-264, 2008.
Wang et al., *Diabetologia*, 50:348-358, 2007.
Wang et al., *J. Biol. Chem.*, 277:17564-17570, 2002.
Wang et al., *Proc. Natl. Acad. Sci. USA*, 106:1427-1432, 2009.
White et al., *Diabetes*, 57:654-668, 2008.
Wicksteed et al., Cell Metab., 5:221-227, 2007.
Wilson et al., *Mech. Dev.*, 120:65-80, 2003.
Xu et al., *J. Biol. Chem.*, 273:4485-4491, 1998.
Zhang et al., *Cell Res.*, 19:429-438, 2009.
Zhou et al., *Nature*, 455:627-632, 2008.

What is claimed is:

1. A method of inducing insulin production and/or secretion from an islet β-cell comprising contacting said cell with a compound of formula (I):

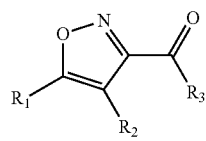

wherein:
R₁ is substituted or unsubstituted phenyl, substituted or unsubstituted thiophenyl or a substituent of formula (A):

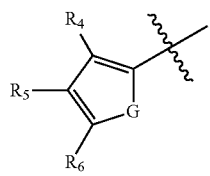

wherein:
R₄, R₅ and R₆ are each independently
hydrogen, hydroxy, halo, cyano, nitro; or
alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and
G is O, —NH, or S;
R₂ is:
hydrogen, hydroxy, halo, or nitro; or
alkyl$_{(C\leq10)}$, alkenyl$_{(C\leq10)}$, alkynyl$_{(C\leq10)}$, alkoxy$_{(C\leq10)}$, alkenyloxy$_{(C\leq10)}$, alkynyloxy$_{(C\leq10)}$, aryl$_{(C\leq12)}$, aralkyl$_{(C\leq15)}$, acyl$_{(C\leq10)}$, or a substituted version of any of these groups; or
—C(O)R₇, —OC(O)R₇, —OC(O)OR₇, —C(O)NR₈R₉, —OC(O)NR₈R₉, —NR₈OR₉, or —SO₃R₇; wherein
R₇ is hydrogen, alkyl$_{(C\leq10)}$, aryl$_{(C\leq12)}$, aralkyl$_{(C\leq15)}$;
R₈ and R₉ are each independently hydrogen, alkyl$_{(C\leq10)}$, aryl$_{(C\leq12)}$, aralkyl$_{(C\leq15)}$, or taken together are alkanediyl$_{(C\leq6)}$;
R₃ is —NH—O-alkyl$_{(C\leq10)}$, —NHOH, —OR₁₀ or —NR₁₁R₁₂, wherein
R₁₀ is hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$;
R₁₁ and R₁₂ are each independently hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$; or
R₁₁ and R₁₂ are taken together to form alkanediyl$_{(C\leq6)}$, —CH₂CH₂NHCH₂CH₂—, or —CH₂CH₂OCH₂CH₂—; or
R₁₁ and R₁₂ are taken together to form alkanediyl$_{(C\leq6)}$;
or pharmaceutically acceptable salt thereof.

2. The method of claim 1, wherein R₁ is a substituent of formula (A).

3. The method of claim 2, wherein G is S.

4. The method of claim 3, wherein R₄, R₅ or R₆ is hydrogen.

5. The method of claim 4, wherein R₄, R₅ and R₆ are each hydrogen.

6. The method according to claim 1, wherein R₂ is hydrogen.

7. The method according to claim 1, wherein R₃ is —NR₁₁R₁₂.

8. The method of claim 7, wherein R₁₁ or R₁₂ is cyclopropyl, cyclobutyl, cyclopentyl or cyclohexyl.

9. The method of claim 8, wherein R₁₁ or R₁₂ is cyclopropyl.

10. The method of claim 1, wherein the compound of formula (I) is further defined as a compound of formula (II):

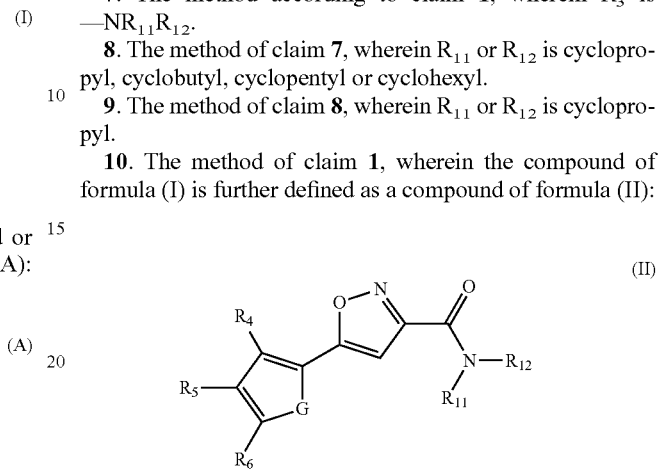

wherein:
R₁₁ and R₁₂ are both hydrogen; or
R₁₁ is hydrogen and R₁₂ is substituted or unsubstituted alkyl$_{(C\leq10)}$, substituted or unsubstituted alkenyl$_{(C\leq10)}$, substituted or unsubstituted alkynyl$_{(C\leq10)}$, or benzyl; or
R₁₁ and R₁₂ taken together are —CH₂CH₂CH₂—, —CH₂CH₂CH₂CH₂—, —CH₂CH₂CH₂CH₂CH₂—, —CH₂CH₂NHCH₂CH₂—, or —CH₂CH₂OCH₂CH₂—;
R₄, R₅ and R₆ are each independently:
hydrogen, halo, hydroxy, cyano, nitro; or
alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and
G is O, NH, or S,
or a pharmaceutically acceptable salt thereof.

11. The method of claim 10, wherein G is S.

12. The method of claim 11, wherein R₄, R₅ or R₆ is hydrogen.

13. The method of claim 12, wherein R₄, R₅ and R₆ are each hydrogen.

14. The method according to claim 1, wherein R₁₁ is hydrogen.

15. The method according to claim 1, wherein R₁₂ is cyclopropyl or an aliphatic$_{(C\leq10)}$ alcohol or an aliphatic$_{(C\leq10)}$ polyol.

16. The method of claim 10, wherein the compound is:

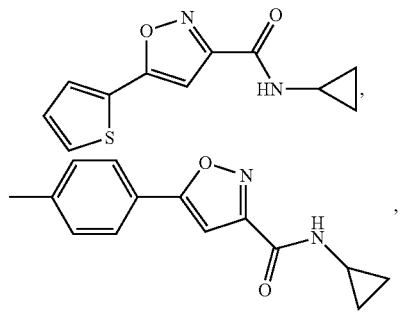

45

-continued

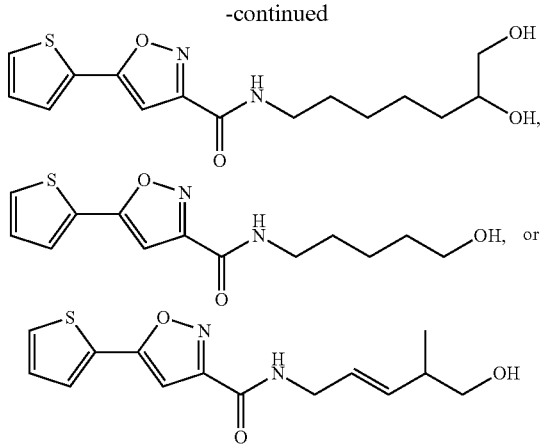

or a pharmaceutically acceptable salt thereof.

17. The method according to claim 1, wherein said cell is located in an animal subject.

18. The method according to claim 1, wherein said cell is contacted ex vivo.

19. A method of treating diabetes in a subject comprising administering to said subject a compound of formula (I):

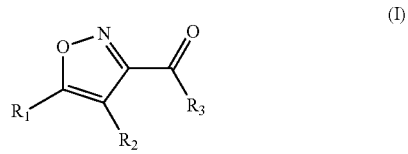

wherein:
R$_1$ is substituted or unsubstituted phenyl, substituted or unsubstituted thiophenyl or a substituent of formula (A):

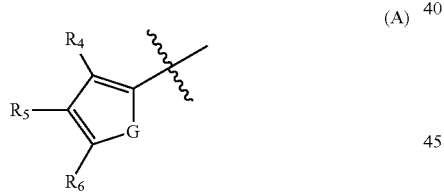

wherein:
R$_4$, R$_5$ and R$_6$ are each independently
hydrogen, hydroxy, halo, cyano, nitro; or
alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and
G is O, —NH, or S;
R$_2$ is:
hydrogen, hydroxy, halo, or nitro; or
alkyl$_{(C\leq10)}$, alkenyl$_{(C\leq10)}$, alkynyl$_{(C\leq10)}$, alkoxy$_{(C\leq10)}$, alkenyloxy$_{(C\leq10)}$, alkynyloxy$_{(C\leq10)}$, aryl$_{(C\leq12)}$, aralkyl$_{(C\leq15)}$, acyl$_{(C\leq10)}$, or a substituted version of any of these groups; or
—C(O)R$_7$, —OC(O)R$_7$, —OC(O)OR$_7$, —C(O)NR$_8$R$_9$, —OC(O)NR$_8$R$_9$, —NR$_8$OR$_9$, or —SO$_3$R$_7$; wherein
R$_7$ is hydrogen, alkyl$_{(C\leq10)}$, aryl$_{(C\leq12)}$, aralkyl$_{(C\leq15)}$;
R$_8$ and R$_9$ are each independently hydrogen, alkyl$_{(C\leq10)}$, aryl$_{(C\leq12)}$, aralkyl$_{(C\leq15)}$, or taken together are alkanediyl$_{(C\leq6)}$;

46

R$_3$ is —NH—O-alkyl$_{(C\leq10)}$, —NHOH, —OR$_{10}$ or —NR$_{11}$R$_{12}$, wherein
R$_{10}$ is hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$;
R$_{11}$ and R$_{12}$ are each independently hydrogen, substituted or unsubstituted alkyl$_{(C\leq10)}$, substituted or unsubstituted alkenyl$_{(C\leq10)}$, substituted or unsubstituted alkynyl$_{(C\leq10)}$, substituted or unsubstituted aryl$_{(C\leq12)}$, or substituted or unsubstituted aralkyl$_{(C\leq15)}$; or
R$_{11}$ and R$_{12}$ are taken together to form alkanediyl$_{(C\leq6)}$, —CH$_2$CH$_2$NHCH$_2$CH$_2$—, or —CH$_2$CH$_2$OCH$_2$CH$_2$—; or
R$_{11}$ and R$_{12}$ are taken together to form alkanediyl$_{(C\leq6)}$; or pharmaceutically acceptable salt thereof.

20. A method of treating diabetes in a subject comprising
(a) contacting an islet β-cell ex vivo with a compound of formula (I):

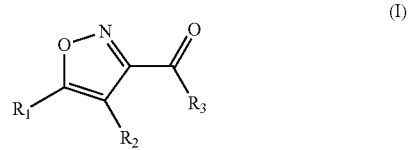

wherein:
R$_1$ is substituted or unsubstituted phenyl, substituted or unsubstituted thiophenyl or a substituent of formula (A):

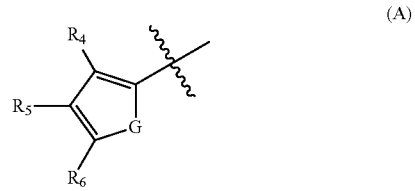

wherein:
R$_4$, R$_5$ and R$_6$ are each independently
hydrogen, hydroxy, halo, cyano, nitro; or
alkyl$_{(C\leq10)}$, aryl$_{(C\leq12)}$, aralkyl$_{(C\leq15)}$, heteroaryl$_{(C\leq12)}$, acyl$_{(C\leq10)}$ or a substituted version of any of these groups; and
G is O, —NH, or S;
R$_2$ is:
hydrogen, hydroxy, halo, or nitro; or
alkyl$_{(C\leq10)}$, alkenyl$_{(C\leq10)}$, alkynyl$_{(C\leq10)}$, alkoxy$_{(C\leq10)}$, alkenyloxy$_{(C\leq10)}$, alkynyloxy$_{(C\leq10)}$, aryl$_{(C\leq12)}$, aralkyl$_{(C\leq15)}$, acyl$_{(C\leq10)}$, or a substituted version of any of these groups; or
—C(O)R$_7$, —OC(O)R$_7$, —OC(O)OR$_7$, —C(O)NR$_8$R$_9$, —OC(O)NR$_8$R$_9$, —NR$_8$OR$_9$, or —SO$_3$R$_7$; wherein
R$_7$ is hydrogen, alkyl$_{(C\leq10)}$, aryl$_{(C\leq12)}$, aralkyl$_{(C\leq15)}$;
R$_8$ and R$_9$ are each independently hydrogen, alkyl$_{(C\leq10)}$, aryl$_{(C\leq12)}$, aralkyl$_{(C\leq15)}$, or taken together are alkanediyl$_{(C\leq6)}$;

$R_3$ is —NH—O-alkyl$_{(C \leq 10)}$, —NHOH, —OR$_{10}$ or —NR$_{11}$R$_{12}$, wherein
  $R_{10}$ is hydrogen, substituted or unsubstituted alkyl$_{(C \leq 10)}$, substituted or unsubstituted alkenyl$_{(C \leq 10)}$, substituted or unsubstituted alkynyl$_{(C \leq 10)}$, substituted or unsubstituted aryl$_{(C \leq 12)}$, or substituted or unsubstituted aralkyl$_{(C \leq 15)}$;
  $R_{11}$ and $R_{12}$ are each independently hydrogen, substituted or unsubstituted alkyl$_{(C \leq 10)}$, substituted or unsubstituted alkenyl$_{(C \leq 10)}$, substituted or unsubstituted alkynyl$_{(C \leq 10)}$, aryl$_{(C \leq 12)}$, or aralkyl$_{(C \leq 15)}$; or
  $R_{11}$ and $R_{12}$ are taken together to form alkanediyl$_{(C \leq 6)}$, —CH$_2$CH$_2$NHCH$_2$CH$_2$—, or —CH$_2$CH$_2$OCH$_2$CH$_2$—; or
  $R_{11}$ and $R_{12}$ are taken together to form alkanediyl$_{(C \leq 6)}$;
or pharmaceutically acceptable salt thereof; and
(b) administering said islet β-cell to said subject.

21. A method of reactivating an islet β-cell comprising contacting said cell with a compound of formula (I):

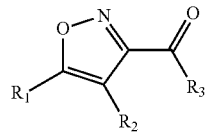
(I)

wherein:
  $R_1$ is substituted or unsubstituted phenyl, substituted or unsubstituted thiophenyl or a substituent of formula (A):

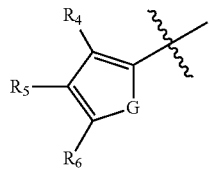
(A)

wherein:
  $R_4$, $R_5$ and $R_6$ are each independently
    hydrogen, hydroxy, halo, cyano, nitro; or
    alkyl$_{(C \leq 10)}$, aryl$_{(C \leq 12)}$, aralkyl$_{(C \leq 15)}$, heteroaryl$_{(C \leq 12)}$, acyl$_{(C \leq 10)}$ or a substituted version of any of these groups; and
  G is O, —NH, or S;
$R_2$ is:
  hydrogen, hydroxy, halo, or nitro; or
  alkyl$_{(C \leq 10)}$, alkenyl$_{(C \leq 10)}$, alkynyl$_{(C \leq 10)}$, alkoxy$_{(C \leq 10)}$, alkenyloxy$_{(C \leq 10)}$, alkynyloxy$_{(C \leq 10)}$, aryl$_{(C \leq 12)}$, aralkyl$_{(C \leq 15)}$, acyl$_{(C \leq 10)}$, or a substituted version of any of these groups; or
  —C(O)R$_7$, —OC(O)R$_7$, —OC(O)OR$_7$, —C(O)NR$_8$R$_9$, —OC(O)NR$_8$R$_9$, —NR$_8$OR$_9$, or —SO$_3$R$_7$; wherein
    $R_7$ is hydrogen, alkyl$_{(C \leq 10)}$, aryl$_{(C \leq 12)}$, aralkyl$_{(C \leq 15)}$;
    $R_8$ and $R_9$ are each independently hydrogen, alkyl$_{(C \leq 10)}$, aryl$_{(C \leq 12)}$, aralkyl$_{(C \leq 15)}$, or taken together are alkanediyl$_{(C \leq 6)}$;
$R_3$ is —NH—O-alkyl$_{(C \leq 10)}$, —NHOH, —OR$_{10}$ or —NR$_{11}$R$_{12}$, wherein
  $R_{10}$ is hydrogen, substituted or unsubstituted alkyl$_{(C \leq 10)}$, substituted or unsubstituted alkenyl$_{(C \leq 10)}$, substituted or unsubstituted alkynyl$_{(C \leq 10)}$, substituted or unsubstituted aryl$_{(C \leq 12)}$, or substituted or unsubstituted aralkyl$_{(C \leq 15)}$;
  $R_{11}$ and $R_{12}$ are each independently hydrogen, substituted or unsubstituted alkyl$_{(C \leq 10)}$, substituted or unsubstituted alkenyl$_{(C \leq 10)}$, substituted or unsubstituted alkynyl$_{(C \leq 10)}$, aryl$_{(C \leq 12)}$, or aralkyl$_{(C \leq 15)}$; or
  $R_{11}$ and $R_{12}$ are taken together to form alkanediyl$_{(C \leq 6)}$, —CH$_2$CH$_2$NHCH$_2$CH$_2$—, or —CH$_2$CH$_2$OCH$_2$CH$_2$—; or
  $R_{11}$ and $R_{12}$ are taken together to form alkanediyl$_{(C \leq 6)}$;
or pharmaceutically acceptable salt thereof.

* * * * *

UNITED STATES PATENT AND TRADEMARK OFFICE
CERTIFICATE OF CORRECTION

PATENT NO. : 8,722,716 B2  
APPLICATION NO. : 13/683907  
DATED : May 13, 2014  
INVENTOR(S) : Elhadij Dioum et al.

Page 1 of 1

It is certified that error appears in the above-identified patent and that said Letters Patent is hereby corrected as shown below:

In title page, item (72) Inventors, delete the 1st inventor "Elhadij Dioum, Dallas, TX (US)" and replace with --Elhadji Dioum, Dallas, TX (US)-- therefor.

In title page, item (56) References Cited - Other Publications, delete the 2nd reference on page 1 "Office Action Issued in U.S. Appl. No. 11/947,479, Dated Aug. 16, 2011." and replace with --Office Action Issued in U.S. Appl. No. 11/974,479, Dated Aug. 16, 2011.-- therefor.

Signed and Sealed this  
Nineteenth Day of August, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,722,716 B2
APPLICATION NO. : 13/683907
DATED : May 13, 2014
INVENTOR(S) : Elhadij Dioum et al.

It is certified that error appears in the above-identified patent and that said Letters Patent is hereby corrected as shown below:

In the Specification

In Column 1, Lines 7-10, delete paragraph and insert:
--This invention was made with government support under grant numbers DK055310 and DK034128 awarded by The National Institutes of Health. The government has certain rights in the invention.--
therefor.

Signed and Sealed this
Seventh Day of July, 2020

Andrei Iancu
*Director of the United States Patent and Trademark Office*

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Synthetic primer

<400> SEQUENCE: 1
cagacctagc accaggg                                                  17

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
ggactttgct gtttgtccc                                                19